United States Patent [19]

Bulla

[11] Patent Number: 6,007,981
[45] Date of Patent: *Dec. 28, 1999

[54] POLYNUCLEOTIDE ENCODING A RECEPTOR FOR A *BACILLUS THURINGIENSIS* TOXIN AND METHODS OF USE

[75] Inventor: Lee A. Bulla, Laramie, Wyo.

[73] Assignee: University of Wyoming, Laramie, Wyo.

[*] Notice: This patent is subject to a terminal disclaimer.

[21] Appl. No.: 08/982,129

[22] Filed: Dec. 10, 1997

Related U.S. Application Data

[62] Division of application No. 08/326,117, Oct. 19, 1994, Pat. No. 5,693,491.

[51] Int. Cl.$^6$ .......................... G01N 33/566; C12N 5/10; C12N 15/11; C07K 14/705

[52] U.S. Cl. ............................. 435/4.2; 435/6; 435/69.1; 435/325; 435/252.3; 435/254.11; 435/320; 435/7.21; 536/23.1; 536/23.5; 530/350; 530/399

[58] Field of Search .................................. 536/23.1, 23.5; 435/69.1, 325, 252.3, 254.11, 320.1, 7.2, 6, 7.21; 530/350, 399; 436/501

[56] References Cited

U.S. PATENT DOCUMENTS

| | | | |
|---|---|---|---|
| 4,675,285 | 6/1987 | Clark et al. | 435/6 |
| 5,071,654 | 12/1991 | English | 424/405 |

FOREIGN PATENT DOCUMENTS

WO 9612964   5/1996   WIPO .

OTHER PUBLICATIONS

Almond et al., Suppression of Protein Structure Destabilizing Mutations in *Bacillus thuringiensis* δ–endotoxin by Second Site Mutations; Biochemistry 32:1040–1046 (1993).
Chen et al., Site–directed mutations in a highly conserved region of *Bacillus thuringiensis* δ–endotoxin affect inhibition of short circuit current across *Bombyx mori* midguts, Proc. Natl. Acad. Sci. USA 90:9041–9045 (1993).
English, L., Mode of action of delta–endotoxins from *Bacillus Thuringiensis*: A comparison with other bacterial toxins, Insect Biochem. Molec. Biol. 22(1):1–7.
Gill et al., The Mode of Action of *BacillusThuringiensis* Endotoxins; Ammu. Rev. Entomol. (1992) 37:615–36.
Hoffman et al., Specificity of *Bacillus Thuringiensis* δ–endotoxins is Correlated with the Presence of High–Affinity Binding Sites in the Brush Border Membrane of Target Insect Midguts; Proc. Natl. Acad. Sci., USA (1988) 85:7844–7848.
Hofte et al., Insecticidal Crystal Proteins of *Bacillus Thuringiensis*; Microbiological Reviews (1989) 53(2):242–255.
Ishihara et al., Molecular cloning and expression of a cDNA encoding the secretin Receptor, EMOB J., vol. 10, No. 7, 1635–1641.

Knight et al., The receptor for *Bacillus thuringiensis* CrylA(c) delta–endotoxin in the brush border membrane of the lepidopteran Manduca sexta is aminopeptidase N, Molecular Microbiology (1994) 11(3):429–436.

Knowles et al., The crystal δ–endotoxins of *Bacillus thuringiensis*: Models for their mechanism of action on the insect gut, BioEssays 15(7):469–476 (1993).

Lee et al., Location of a *Bombyx mori* Receptor Binding Region on a *Bacillus thuringiensis* δ–Endotoxin, J. Biol. Chem., vol. 167, No. 5, pp. 3115–3121 (1992).

Sanchis et al., Identification and partial purification of a *Bacillus thuringiensis* CryIC δ–endotoxin binding protein from *Spodoptera littoralis* gut membrances, FEBS 316(3):264–268 (1993).

Sangadala et al., A Mixture of Manduca Sectra Aminopeptidase and Phosphatase Enhances *Bacillus Thuringiensis* Insecticidal CrylA(c) Toxin Binding and $Rb^+$–$K^+$Efflux in vitro, vol. 269, No. 13, pp. 10088–10092 (1994).

Vadlamudi et al., A Specific Binding Protein from Manduca Sexta for the Insecticidal Toxin of *Bacillus Thuringiensis* Subsp., *Berliner*; J. Biol. Chem. 268(17):12334–12340 (1993).

Van Rie et al., Specificity of *Bacillus Thuringiensis* δ–endotoxins; Eur. J. Biochem. (1989) 186:239–247.

Van Rie et al., Receptors on the Brush Border Membrane of the Insect Midgut as Determinants of the Specificity of *Bacillus Thuringiensis* Belta–Endotoxins (1990) 56(5):1378–1385.

Vadlamundi, R.K., "Cloning and expression of a receptor for an insecticidal toxin of *Bacillus thuringiensis*", J. Biol. Chem., vol. 270, No. 10, Mar. 10, 1995, pp. 5490–5494.

Dorsch, J. A. et al., "Determination of the specific region of BT–R1 to which the CryaAb toxin of *Bacillus thuringiensis* subsp. *Berliner* binds", FASEB Journal (Abstracts), vol. 11, No. 9, Jul. 31, 1997, p. A1050.

*Primary Examiner*—Lorraine Spector
*Assistant Examiner*—Claire M. Kaufman
*Attorney, Agent, or Firm*—Morrison & Foerster LLP

[57] ABSTRACT

The cDNA that encodes a glycoprotein receptor from the tobacco hornworm which binds a *Bacillus thuringiensis* toxin has been obtained and sequenced. The availability of this cDNA permits the retrieval of DNAs encoding homologous receptors in other insects and organisms as well as the design of assays for the cytotoxicity and binding affinity of potential pesticides and the development of methods to manipulate natural and/or introduced homologous receptors and, thus, to destroy target cells, tissues and/or organisms.

4 Claims, 14 Drawing Sheets

FIG. 1A

```
         10          20          30          40          50          60          70          80          90         100         110         120
GACCAATCGGAGTGTGGTGAATTTTTGGAAATATTTTGTGCGGTTCCTTTAGTTGTGTAATATAGTACTTTAGTTACAAATTGGAATAATTGGCAGCAAAACCATCTGCAGCAACAA 130         140         150         160         170         180         190         200         210         220
AATCATCTGCAGCTGCGAAATCATCTGCAGCAGCAAAAGCATCTTCAGGAGCAGAAAAGCCCCAAATAATGTGAG ATG GCA GTT GAC GTC CGA ATC GCT GCC TTC CTG
                                                                               Met Ala Val Asp Val Arg Ile Ala Ala Phe Leu>

230         240         250         260         270         280         290         300         310
CTG GTG TTT ATA GCG CCT GCA GTT TTA GCT CAA GAG AGA TGT GGG TAT ATG ACC GCC ATC CCA CGA CCG GAT AAT TTG CCA
Leu Val Phe Ile Ala Pro Ala Val Leu Ala Gln Glu Arg Cys Gly Tyr Met Thr Ala Ile Pro Arg Pro Asp Asn Leu Pro>

320         330         340         350         360         370         380         390         400
GTA CTA AAT TTT GAA GGC CAG CAG ACA TGG CCC CTG CTC CCC CCG GAG CGG GAT GAC CTG TGC ATG GAC GCC TAC CAC GTG
Val Leu Asn Phe Glu Gly Gln Gln Thr Trp Pro Leu Leu Pro Ala Pro Glu Arg Asp Asp Leu Cys Met Asp Ala Tyr His Val>

410         420         430         440         450         460         470         480         490
ATA ACA GCC AAC CTC GGC ACG CAG ATC TAC ATG GAT GAA GAG ATA GAA GAC GAA ATC ACC ATC GCC ATA CTT AAT TAT AAC GGA CCA
Ile Thr Ala Asn Leu Gly Thr Gln Ile Tyr Met Asp Glu Glu Ile Glu Asp Glu Ile Thr Ile Ala Ile Leu Asn Tyr Asn Gly Pro>

500         510         520         530         540         550         560         570         580
TCA ACT CCG TTC ATT GAA CTG CCA TTT TTA TCC TCG TAC TCG CTG CTG ATG CCG GTC ATC AGG AGA GTT GAC AAC AGT GCA TCT
Ser Thr Pro Phe Ile Glu Leu Pro Phe Leu Ser Ser Tyr Ser Leu Leu Met Pro Val Ile Arg Arg Val Asp Asn Ser Ala Ser>

590         600         610         620         630         640         650         660         670
CAT CAT CAC AGA CAG CAT TAC GAG TTG CCC GGC ATG CAG CAG TAC ATG TTC AAT GTG CGC GTG GAC GGC CAG TCG CTG GCA GGC
His His His Arg Gln His Tyr Glu Leu Pro Gly Met Gln Gln Tyr Met Phe Asn Val Arg Val Asp Gly Gln Ser Leu Ala Gly>

680         690         700         710         720         730         740         750         760
GTG TCT CTC GCT ATC GTC AAC ATA GAT GAC AAC GCG CCC ATC ATA CAA AAC TTC GAG CCT TGC CGG GTT CCT GAA CTG GGC GAG CCA GGG
Val Ser Leu Ala Ile Val Asn Ile Asp Asp Asn Ala Pro Ile Ile Gln Asn Phe Glu Pro Cys Arg Val Pro Glu Leu Gly Glu Pro Gly>
```

FIG. 1B

```
770         780         790         800         810         820         830         840         850
TTG ACA GAA TGC ACA TAC CAA GTA TCG GAC GCG GAC GGA CGG ATC AGC ACA GAG TTC ATG ACG TTC AGG ATC GAC AGC GTT CGT GGC GAC
Leu Thr Glu Cys Thr Tyr Gln Val Ser Asp Ala Asp Gly Arg Ile Ser Thr Glu Phe Met Thr Phe Arg Ile Asp Ser Val Arg Gly Asp 860         870         880         890         900         910         920         930         940
GAG ACC TTC TAC ATC TAC GAA CGG ACG AAT ATC CCC AAC CAA TGG ATG TGG CTA AAT ATG ACC ATA GGC GTT AAT ACC TCG CTC AAC TTC
Glu Thr Phe Tyr Ile Tyr Glu Arg Thr Asn Ile Pro Asn Gln Trp Met Trp Leu Asn Met Thr Ile Gly Val Asn Thr Ser Leu Asn Phe 950         960         970         980         990         1000        1010        1020        1030
GTC ACC AGT CCG CTG CAT ATA TTC AGC ACA GTG TCT GAC TCG CTC CCG AAC ACC CAC ACG GTG ACT ATG GTG CAA GTG GCG AAT
Val Thr Ser Pro Leu His Ile Phe Ser Thr Val Thr Asp Ser Leu Pro Asn Thr His Thr Val Thr Met Val Gln Val Ala Asn 1040        1050        1060        1070        1080        1090        1100        1110        1120
GTG AAC AGC CGT CCG CCG TGG CTG GCT GTC CAA CAG TTT GAA GAG ATC CAA AAC TTC ACA GTG AGG GCG ATC
Val Asn Ser Arg Pro Pro Trp Leu Gly Val Gln Gln Phe Glu Glu Ile Gln Asn Phe Thr Val Arg Ala Ile 1130        1140        1150        1160        1170        1180        1190        1200        1210
GAC GGA GAC ACT GAG ATC AAT ATG CCT ATC AAC TAC AGG CTG ACA AAT GAG GAA GAC ACA TTC AGC ATT GAG GCC CTG CCT GGT
Asp Gly Asp Thr Glu Ile Asn Met Pro Ile Asn Tyr Arg Leu Thr Asn Glu Glu Asp Thr Phe Ser Ile Glu Ala Leu Pro Gly 1220        1230        1240        1250        1260        1270        1280        1290        1300
GTG AAC AGC CGT TTC CTC GTG TTC CTC GTG GCT GTA TTC CTC GTG TCG CCA ATT GAC CGC GAC ACA CTG CAA CGA GAG TTT CCA CTT ACG ATC GTC GCT TAC AAA
Val Asn Ser Arg Phe Leu Val Phe Leu Val Ala Val Phe Leu Val Ser Pro Ile Asp Arg Asp Thr Leu Gln Arg Glu Phe Pro Leu Thr Ile Val Ala Tyr Lys 1310        1320        1330        1340        1350        1360        1370        1380        1390
GGA AAA AGC GGG GCT GTA TTC CTC ACA TCA ACA AAC GTG GTC ATC ATT GTG ACA GAC ATC GAA CAA CCT GAA CCT ATA CAC AAG GAA
Gly Lys Ser Gly Ala Val Phe Leu Thr Ser Thr Asn Val Val Ile Ile Val Thr Asp Ile Asn Asp Gln Arg Pro Glu Pro Ile His Lys Glu 1400        1410        1420        1430        1440        1450        1460        1470        1480
TAT CGA CTG GCA ATC ATG GAG GAG ACG CCC CTG ACC CTC AAC TTC GAT AAA GAA TTC CAT GAT AAG GAT TTA GGT CAA AAC GCT
Tyr Arg Leu Ala Ile Met Glu Glu Thr Pro Leu Thr Leu Asn Phe Asp Lys Glu Phe His Asp Lys Asp Leu Gly Gln Asn Ala
```

```
2210                2220                2230                2240                2250                2260                2270                2280                2290
CAG GCT AAC CCC GAC GAG TTT AGG AAT TGC GTG GAA ATC ATC GAG ACC TTC CCC GAG ATT AAC AAC CGG GGA CTG GCT ATC GGC CGC GTT
Gln Ala Asn Pro Asp Glu Phe Arg Asn Cys Val Glu Ile Ile Glu Thr Phe Pro Glu Ile Asn Asn Arg Gly Leu Ala Ile Gly Arg Val>

2300                2310                2320                2330                2340                2350                2360                2370                2380
GTA GCG CGC GAA ATC AGA CAC AAC GTG ACC ATA GAC TAC GAG GAG TTT GAG GTC CTC ACA TCC CTC ACA GTG AGG GTG CGT GAC CTT AAC ACC
Val Ala Arg Glu Ile Arg His Asn Val Thr Ile Asp Tyr Glu Glu Phe Glu Val Leu Thr Ser Leu Thr Val Arg Val Arg Asp Leu Asn Thr>

2390                2400                2410                2420                2430                2440                2450                2460                2470
GTC TAC GGA GAC GAC TAC GAC GAA TCG ATG ATG CTC ACA ATA ACT ATC GAT ATG AAC GAC GCG CCG GTG TGG GAG GGG ACT CTG
Val Tyr Gly Asp Asp Tyr Asp Glu Ser Met Met Leu Thr Ile Thr Ile Asp Met Asn Asp Ala Pro Val Trp Glu Gly Thr Leu>

2480                2490                2500                2510                2520                2530                2540                2550                2560
GAG CAG AAC TTC CGA GTC CGC CGC GAG ATG GGC GGG GGC GTC GTG GTG GGC TCC GTG CGC GAC GAC ATC GAC GGA CCG CTC TAC AAC
Glu Gln Asn Phe Arg Val Arg Arg Glu Met Gly Gly Gly Val Val Val Gly Ser Val Arg Asp Asp Ile Asp Gly Pro Leu Tyr Asn>

2570                2580                2590                2600                2610                2620                2630                2640                2650
CAA GTG CGA TAC ACC ATT TTC CCT CGT GAA GAC ACA ACT GAT AAG GAC CTG ATA ATG ATC CTC ACG GGT CAA ATT TCC AAC ACA
Gln Val Arg Tyr Thr Ile Phe Pro Arg Glu Asp Thr Thr Asp Lys Asp Leu Ile Met Ile Leu Thr Gly Gln Ile Ser Val Asn Thr>

2660                2670                2680                2690                2700                2710                2720                2730                2740
AGC GGC GCC ATC GAC GCG GAT ACT CCA CGC TTC CAC CTC TAC TAT ACA GTG GTC GCT AGT GAC TGC TCG ACA GAA GAT CCT GCA
Ser Gly Ala Ile Asp Ala Asp Thr Pro Arg Phe His Leu Tyr Tyr Tyr Thr Val Val Ala Ser Asp Arg Cys Ser Thr Glu Asp Pro Ala>

2750                2760                2770                2780                2790                2800                2810                2820                2830                2840                2850
GAT TGC CCC CCT GAC CCG ACT TAT TGG GAA ACC AAT ATC ACA CAC ATC ACC GAC GAC AAC ACG AAC AAC AAG GTC CCG CAG GCG GAA
Asp Cys Pro Pro Asp Pro Thr Tyr Trp Glu Thr Asn Ile Thr His Ile Thr Asp Asp Asn Thr Asn Asn Lys Val Pro Gln Ala Glu>

2840                2850                2860                2870                2880                2890                2900                2910                2920
ACG ACT AAG TTC GAT ACC GTC GTG TAT ATT TAC GAG GTC GCA ACC CAC TTA GAC GAG GTG ACT CTG ATA GCC AGT GAT CTT GAC AGA
Thr Thr Lys Phe Asp Thr Val Val Tyr Ile Tyr Glu Val Ala Thr His Leu Asp Glu Val Thr Leu Ile Ala Ser Asp Leu Asp Arg>
```

FIG. 1E

```
2930  GAC GAA ATA CAC ACG GTG AGC TAC GTC ATC AAT TAT GCA GTG AAC CCT CGA CTG ATG AAC TTC TCC GTG AAC CGA GAG ACC GGC
      Asp Glu Ile His Thr Val Ser Tyr Val Ile Asn Tyr Ala Val Asn Pro Arg Leu Met Asn Phe Ser Val Asn Arg Glu Thr Gly>

3020  CTG GTG TAC GTG GAC TAT GAG ACC CAG ACC GGT AGT GGC GAG CAG CTG GAT GGT CGT GAT GAA CCA ACG CGT ATC TTC TTC AAC CTC
      Leu Val Tyr Val Asp Tyr Glu Thr Gln Thr Gly Ser Gly Glu Gln Leu Asp Gly Arg Asp Glu Pro Thr Arg Ile Phe Phe Asn Leu>

3110  ATC GAC AAC TTC ATG GGG GAA GGA GAA GAA AAT CAG AAC AGA ACA GAA GTT CTC GTT ATC TTG GAT GTG AAT GCT
      Ile Asp Asn Phe Met Gly Glu Gly Glu Glu Asn Gln Asn Arg Thr Glu Val Leu Val Ile Leu Asp Val Asn Ala>

3200  CCT GAA TTG CCA CCG CCG AGC AGC GAA CTC CTC ATA TCT ACT ATA TCT GAG AAC CTT AAG CAG GGC GTC CGT GAA CAG CAT ATC TTC GCC CCG
      Pro Glu Leu Pro Pro Pro Ser Ser Glu Leu Leu Ile Ser Thr Ile Ser Glu Asn Leu Lys Gln Gly Val Arg Glu Gln His Ile Phe Ala Pro>

3290  GAC CGC GAC GAG CCC GAC ACA AAC TCC GTC AGG AGC TAC ATC CTG GAG GAC CGG AGC ATG GAC CTC GAA GTG CCG GAG CTG
      Asp Arg Asp Glu Pro Asp Thr Asn Ser Val Arg Ser Tyr Ile Leu Glu Asp Arg Ser Met Asp Leu Glu Val Pro Glu Leu>

3380  TTT GTG ATA CAG ATC GCG AAC GTC ACG GGA GAG CTG ACC ATG GAC CTC AAG GGA TAT TGG ACG TAC GCT ATA CAT ATA
      Phe Val Ile Gln Ile Ala Asn Val Thr Gly Glu Leu Thr Met Asp Leu Lys Gly Tyr Trp Thr Tyr Ala Ile His Ile>

3470  CGG GCA TTC GAC CAC GGC ATT CCG CAA ATG TCC ATG AAC GAG ACA TAT TGC ATC ATC CCG TTC AAC CAT CCT GAG TTC
      Arg Ala Phe Asp His Gly Ile Pro Gln Met Ser Met Asn Glu Thr Tyr Leu Glu Ile Ile Pro Phe Asn His Pro Glu Phe>

3560  GTC TTC CCG ACC GAT GCC AAC GAT GTC ATA CGA GCG AGG CGA CTT GTA ATC AAT GGA GTT CTA GCG ACA GTG AAC GGA GAG TTC TTG
      Val Phe Pro Thr Asp Ala Asn Asp Val Ile Arg Ala Arg Arg Leu Val Ile Asn Gly Val Leu Ala Thr Val Asn Gly Glu Phe Leu>
```

```
3650                3660            3670            3680            3690            3700            3710            3720            3730
GAG CGG ATA TCG GCG ACT GAT CCG GAC CTC CAC GCG GGC GTC GTC ACC TTC CAA GAG GAT GAG TCA CAA CGG TAC TTT
Glu Arg Ile Ser Ala Thr Asp Pro Asp Leu His Ala Gly Val Val Thr Phe Gln Glu Asp Glu Ser Gln Arg Tyr Phe>

3740                3750            3760            3770            3780            3790            3800            3810            3820
CAA GTT AAC GAT GGC GAG AAC CTC GGC TCG TTG AGG TTA CTG CAA GCC GTT CCA GAG GAG ATC AGG GAG TTC CGG ATA ACG ATT CGC
Gln Val Asn Asp Gly Glu Asn Leu Gly Ser Leu Arg Leu Leu Gln Ala Val Pro Glu Glu Ile Arg Glu Phe Arg Ile Thr Ile Arg>

3830                3840            3850            3860            3870            3880            3890            3900            3910
GCT ACA GAC CAG GGA GAC CCG CTG TCC ACG GAC ATG ACG TTC AGA GTT GTT TTT GTG CCC ACG CAA GAA CCT AGA TTC
Ala Thr Asp Gln Gly Asp Pro Leu Ser Thr Asp Met Thr Phe Arg Val Val Phe Val Pro Thr Gln Glu Pro Arg Phe>

3920                3930            3940            3950            3960            3970            3980            3990            4000
GCG TCC TCA GAA CAT GTC TTC GCT ATA GAA AAG AGT GCC GGC ATG GAA GAG TCT CAC CAA CTT CCT CTA GCA GAC ATC AAG AAC
Ala Ser Glu His Val Phe Ala Ile Glu Lys Ser Ala Gly Met Glu Glu Ser His Gln Leu Pro Leu Ala Asp Ile Lys Asn>

4010                4020            4030            4040            4050            4060            4070            4080            4090
CAT CTC TGT GAA GAC GAC ATT TAC AGC ATT TAC TAT CGT ATT ATC GAT GGC AAC AGC GAA GGT CAT TTC GGC CTG GAT CCT GTT CGC
His Leu Cys Glu Asp Asp Cys His Ser Ile Tyr Tyr Arg Ile Ile Asp Gly Asn Ser Glu Gly His Phe Gly Leu Asp Pro Val Arg>

4100                4110            4120            4130            4140            4150            4160            4170            4180
AGG TTG TTC CTG AAG AAA GAG ATA AGG GAA CAA GCC TCC ACT CAC GTG GCG GCT AGT AAC TCG CCC GAT GGT GGC ATT
Arg Leu Phe Leu Lys Lys Glu Ile Arg Glu Gln Ala Ser Thr His Val Ala Ala Ser Asn Ser Pro Asp Gly Gly Ile>

4190                4200            4210            4220            4230            4240            4250            4260            4270
CCA CTT CCT TCC ATC CTT ACT GTC ACC GTT ACC GTG AGG GAG GCA GAC CCT CGT CCA GTG TTT GTG AGG GAA TTG TAC ACC GCA GGG
Pro Leu Pro Ser Ile Leu Thr Val Thr Val Thr Val Arg Arg Glu Ala Asp Pro Arg Pro Val Phe Val Arg Glu Leu Tyr Thr Ala Gly>

4280                4290            4300            4310            4320            4330            4340            4350            4360
ATA TCC ACA GCG GAC TCC ATC AGA AGA AGG AGA GAG CTC CTC CTC AGA TTA CAT GCG ACC CAG TCT GAA GGC TCG GCC ATT ACT TAT GCT ATA GAC TAC
Ile Ser Thr Ala Asp Ser Ile Arg Arg Arg Arg Glu Leu Leu Leu Arg Leu His Ala Thr Gln Ser Glu Gly Ser Ala Ile Thr Tyr Ala Ile Asp Tyr>
```

```
        5200      5210      5220      5230      5240      5250      5260      5270      5280      5290      5300      5310
         *         *         *         *         *         *         *         *         *         *         *         *
GAAGATCTTGCGCACTTTGGCAACGTCTTCATGGATCCTGAGGTGAACGAAAAGGCAAATGGTTATCCCGAAGTCGCAAACCACAACAACTTCGCTTTCAACCGACTCCCTTCTCG 5320      5330      5340      5350      5360      5370      5380      5390      5400      5410      5420      5430
         *         *         *         *         *         *         *         *         *         *         *         *
CCTGAGTTCGTTAACGGACAGTTCAGAAGATCTAGAAGATAACAACACTAGTTAAGATCATTAATTTTGGAGTTTGGAATTAAGATTTTTGAAAGGATAGTTGTGATAAGCCTGTGATT 5440      5450      5460      5470      5480      5490      5500      5510      5520      5530      5540      5550
         *         *         *         *         *         *         *         *         *         *         *         *
TTTAAAACTGTAATTGAAAAAAAAATTGAGACCTCCATTTAAGCTCTTGCTCTCATCTCATCAAATTTTATAAAATGCCATTAGTCATTAAGATACTGATTAATTAAGATTATTTA 5560      5570
         *         *
AGATATTATGTAAAATAAATATTGTC
```

FIG. 1H

Met Ala Val Asp Val Arg Ile Ala Ala Phe Leu Leu Val Phe Ile Ala
1           5                   10                  15

Pro Ala Val Leu Ala Gln Glu Arg Cys Gly Tyr Met Thr Ala Ile Pro
            20                  25                  30

Arg Leu Pro Arg Pro Asp Asn Leu Pro Val Leu Asn Phe Glu Gly Gln
        35                  40                  45

Thr Trp Ser Gln Arg Pro Leu Leu Pro Ala Pro Glu Arg Asp Asp Leu
    50                  55                  60
                            ┌─── Cad1 ──────────▶

Cys Met Asp Ala Tyr His Val Ile Thr Ala Asn Leu Gly Thr Gln Val
65                  70                  75                  80

Ile Tyr Met Asp Glu Glu Ile Glu Asp Glu Ile Thr Ile Ala Ile Leu
            85                  90                  95

Asn Tyr Asn Gly Pro Ser Thr Pro Phe Ile Glu Leu Pro Phe Leu Ser
            100                 105                 110

Gly Ser Tyr Asn Leu Leu Met Pro Val Ile Arg Arg Val Asp Asn Gly
        115                 120                 125

Ser Ala Ser His His His Ala Arg Gln His Tyr Glu Leu Pro Gly Met
    130                 135                 140

Gln Gln Tyr Met Phe Asn Val Arg Val Asp Gly Gln Ser Leu Val Ala
145             150                 155                 160

Gly Val Ser Leu Ala Ile Val Asn Ile Asp Asp Asn Ala Pro Ile Ile
                165                 170                 175
┌─── Cad2 ──────▶

Gln Asn Phe Glu Pro Cys Arg Val Pro Glu Leu Gly Glu Pro Gly Leu
            180                 185                 190

Thr Glu Cys Thr Tyr Gln Val Ser Asp Ala Asp Gly Arg Ile Ser Thr
        195                 200                 205

Glu Phe Met Thr Phe Arg Ile Asp Ser Val Arg Gly Asp Glu Glu Thr
    210                 215                 220

Phe Tyr Ile Glu Arg Thr Asn Ile Pro Asn Gln Trp Met Trp Leu Asn
225                 230                 235                 240

Met Thr Ile Gly Val Asn Thr Ser Leu Asn Phe Val Thr Ser Pro Leu
                245                 250                 255

His Ile Phe Ser Val Thr Ala Leu Asp Ser Leu Pro Asn Thr His Thr
        260                 265                 270

Val Thr Met Met Val Gln Val Ala Asn Val Asn Ser Arg Pro Pro Arg
        275                 280                 285

FIG. 2A

```
                    Cad3
        Trp Leu Glu Ile Phe Ala Val Gln Gln Phe Glu Glu Lys Ser Tyr Gln
            290             295             300
        Asn Phe Thr Val Arg Ala Ile Asp Gly Asp Thr Glu Ile Asn Met Pro
        305             310             315             320
        Ile Asn Tyr Arg Leu Ile Thr Asn Glu Glu Asp Thr Phe Phe Ser Ile
                        325             330             335
        Glu Ala Leu Pro Gly Gly Lys Ser Gly Ala Val Phe Leu Val Ser Pro
                    340             345             350
        Ile Asp Arg Asp Thr Leu Gln Arg Glu Val Phe Pro Leu Thr Ile Val
                355             360             365
        Ala Tyr Lys Tyr Asp Glu Glu Ala Phe Ser Thr Ser Thr Asn Val Val
            370             375             380
                                                            Cad4
        Ile Ile Val Thr Asp Ile Asn Asp Gln Arg Pro Glu Pro Ile His Lys
        385             390             395             400
        Glu Tyr Arg Leu Ala Ile Met Glu Glu Thr Pro Leu Thr Leu Asn Phe
                        405             410             415
        Asp Lys Glu Phe Gly Phe His Asp Lys Asp Leu Gly Gln Asn Ala Gln
                    420             425             430
        Tyr Thr Val Arg Leu Glu Ser Val Asp Pro Pro Gly Ala Ala Glu Ala
                435             440             445
        Phe Tyr Ile Ala Pro Glu Val Gly Tyr Gln Arg Gln Thr Phe Ile Met
            450             455             460
        Gly Thr Leu Asn His Ser Met Leu Asp Tyr Glu Val Pro Glu Phe Gln
        465             470             475             480
        Ser Ile Thr Ile Arg Val Val Ala Thr Asp Asn Asn Asp Thr Arg His
                        485             490             495
                    Cad5
        Val Gly Val Ala Leu Val His Ile Asp Leu Ile Asn Trp Asn Asp Glu
                    500             505             510
        Gln Pro Ile Phe Glu His Ala Val Gln Thr Val Thr Phe Asp Glu Thr
                515             520             525
        Glu Gly Glu Gly Phe Phe Val Ala Lys Ala Val Ala His Asp Arg Asp
            530             535             540
        Ile Gly Asp Val Val Glu His Thr Leu Leu Gly Asn Ala Val Asn Phe
        545             550             555             560
```

FIG. 2B

```
Leu Thr Ile Asp Lys Leu Thr Gly Asp Ile Arg Val Ser Ala Asn Asp
                 565             570             575
Ser Phe Asn Tyr His Arg Glu Ser Glu Leu Phe Val Gln Val Arg Ala
             580             585             590
Thr Asp Thr Leu Gly Glu Pro Phe His Thr Ala Thr Ser Gln Leu Val
         595             600             605
                                                        ┌Cad6──►
Ile Arg Leu Asn Asp Ile Asn Asn Thr Pro Pro Thr Leu Arg Leu Pro
     610             615             620
Arg Gly Ser Pro Gln Val Glu Glu Asn Val Pro Asp Gly His Val Ile
625             630             635                         640
Thr Gln Glu Leu Arg Ala Thr Asp Pro Asp Thr Thr Ala Asp Leu Arg
                 645             650             655
Phe Glu Ile Asn Trp Asp Thr Ser Phe Ala Thr Lys Gln Gly Arg Gln
             660             665             670
Ala Asn Pro Asp Glu Phe Arg Asn Cys Val Glu Ile Glu Thr Ile Phe
         675             680             685
Pro Glu Ile Asn Asn Arg Gly Leu Ala Ile Gly Arg Val Val Ala Arg
     690             695             700
Glu Ile Arg His Asn Val Thr Ile Asp Tyr Glu Glu Phe Glu Val Leu
705             710             715                         720
Ser Leu Thr Val Arg Val Arg Asp Leu Asn Thr Val Tyr Gly Asp Asp
                 725             730             735
Tyr Asp Glu Ser Met Leu Thr Ile Thr Ile Ile Asp Met Asn Asp Asn
             740             745             750
         ┌──CAD7─────────────────►
Ala Pro Val Trp Val Glu Gly Thr Leu Glu Gln Asn Phe Arg Val Arg
         755             760             765
Glu Met Ser Ala Gly Gly Leu Val Val Gly Ser Val Arg Ala Asp Asp
     770             775             780
Ile Asp Gly Pro Leu Tyr Asn Gln Val Arg Tyr Thr Ile Phe Pro Arg
785             790             795                         800
Glu Asp Thr Asp Lys Asp Leu Ile Met Ile Asp Phe Leu Thr Gly Gln
                 805             810             815
Ile Ser Val Asn Thr Ser Gly Ala Ile Asp Ala Asp Thr Pro Pro Arg
             820             825             830
Phe His Leu Tyr Tyr Thr Val Val Ala Ser Asp Arg Cys Ser Thr Glu
         835             840             845
```

FIG. 2C

Asp Pro Ala Asp Cys Pro Pro Asp Pro Thr Tyr Trp Glu Thr Glu Gly
    850             855             860

Asn Ile Thr Ile His Ile Thr Asp Thr Asn Asn Lys Val Pro Gln Ala
865             870             875             880
    Cad8 ──────▶

Glu Thr Thr Lys Phe Asp Thr Val Val Tyr Ile Tyr Glu Asn Ala Thr
            885             890             895

His Leu Asp Glu Val Val Thr Leu Ile Ala Ser Asp Leu Asp Arg Asp
        900             905             910

Glu Ile Tyr His Thr Val Ser Tyr Val Ile Asn Tyr Ala Val Asn Pro
    915             920             925

Arg Leu Met Asn Phe Phe Ser Val Asn Arg Glu Thr Gly Leu Val Tyr
    930             935             940

Val Asp Tyr Glu Thr Gln Gly Ser Gly Glu Val Leu Asp Arg Asp Gly
945             950             955             960

Asp Glu Pro Thr His Arg Ile Phe Phe Asn Leu Ile Asp Asn Phe Met
            965             970             975

Gly Glu Gly Glu Gly Asn Arg Asn Gln Asn Asp Thr Glu Val Leu Val
        980             985             990
                                            Cad9 ──────▶

Ile Leu Leu Asp Val Asn Asp Asn Ala Pro Glu Leu Pro Pro Pro Ser
    995             1000            1005

Glu Leu Ser Trp Thr Ile Ser Glu Asn Leu Lys Gln Gly Val Arg Leu
    1010            1015            1020

Glu Pro His Ile Phe Ala Pro Asp Arg Asp Glu Pro Asp Thr Asp Asn
1025            1030            1035            1040

Ser Arg Val Gly Tyr Glu Ile Leu Asn Leu Ser Thr Glu Arg Asp Ile
            1045            1050            1055

Glu Val Pro Glu Leu Phe Val Met Ile Gln Ile Ala Asn Val Thr Gly
        1060            1065            1070

Glu Leu Glu Thr Ala Met Asp Leu Lys Gly Tyr Trp Gly Thr Tyr Ala
    1075            1080            1085

Ile His Ile Arg Ala Phe Asp His Gly Ile Pro Gln Met Ser Met Asn
    1090            1095            1100

Glu Thr Tyr Glu Leu Ile Ile His Pro Phe Asn Tyr Tyr Ala Pro Glu
1105            1110            1115            1120

FIG. 2D

```
┌─Cad10──────────────▶
Phe Val Phe Pro Thr Asn Asp Ala Val Ile Arg Leu Ala Arg Glu Arg
              1125            1130              1135
Ala Val Ile Asn Gly Val Leu Ala Thr Val Asn Gly Glu Phe Leu Glu
            1140            1145            1150
Arg Ile Ser Ala Thr Asp Pro Asp Gly Leu His Ala Gly Val Val Thr
            1155            1160            1165
Phe Gln Val Val Gly Asp Glu Glu Ser Gln Arg Tyr Phe Gln Val Val
    1170            1175            1180
Asn Asp Gly Glu Asn Leu Gly Ser Leu Arg Leu Leu Gln Ala Val Pro
1185            1190            1195            1200
Glu Glu Ile Arg Glu Phe Arg Ile Thr Ile Arg Ala Thr Asp Gln Gly
                1205            1210            1215
Thr Asp Pro Gly Pro Leu Ser Thr Asp Met Thr Phe Arg Val Val Phe
            1220            1225            1230
                                    ┌─Cad11──────────────▶
Val Pro Thr Gln Gly Glu Pro Arg Phe Ala Ser Ser Glu His Ala Val
        1235            1240            1245
Ala Phe Ile Glu Lys Ser Ala Gly Met Glu Glu Ser His Gln Leu Pro
    1250            1255            1260
Leu Ala Gln Asp Ile Lys Asn His Leu Cys Glu Asp Asp Cys His Ser
1265            1270            1275            1280
Ile Tyr Tyr Arg Ile Ile Asp Gly Asn Ser Glu Gly His Phe Gly Leu
            1285            1290            1295
Asp Pro Val Arg Asn Arg Leu Phe Leu Lys Lys Glu Leu Ile Arg Glu
        1300            1305            1310
Gln Ser Ala Ser His Thr Leu Gln Val Ala Ala Ser Asn Ser Pro Asp
        1315            1320            1325
Gly Gly Ile Pro Leu Pro Ala Ser Ile Leu Thr Val Thr Val Thr Val
    1330            1335            1340
Arg Glu Ala Asp Pro Arg Pro Val Phe Val Arg Glu Leu Tyr Thr Ala
1345            1350            1355            1360
Gly Ile Ser Thr Ala Asp Ser Ile Gly Arg Glu Leu Leu Arg Leu His
            1365            1370            1375
Ala Thr Gln Ser Glu Gly Ser Ala Ile Thr Tyr Ala Ile Asp Tyr Asp
            1380            1385            1390
```

FIG. 2E

Thr Met Val Val Asp Pro Ser Leu Glu Ala Val Arg Gln Ser Ala Phe
        1395            1400              1405

Val Leu Asn Ala Gln Thr Gly Val Leu Thr Leu Asn Ile Gln Pro Thr
    1410            1415              1420

Ala Thr Met His Gly Leu Phe Lys Phe Glu Val Thr Ala Thr Asp Thr
1425            1430              1435              1440

Ala Gly Ala Gln Asp Arg Thr Asp Val Thr Val Tyr Val Val Ser Ser
                1445              1450              1455

Gln Asn Arg Val Tyr Phe Val Phe Val Asn Thr Leu Gln Gln Val Glu
            1460              1465              1470

Asp Asn Arg Asp Phe Ile Ala Asp Thr Phe Ser Ala Gly Phe Asn Met
            1475              1480              1485

Thr Cys Asn Ile Asp Gln Val Val Pro Ala Asn Asp Pro Val Thr Gly
    1490              1495              1500

Val Ala Leu Glu His Ser Thr Gln Met Ala Ala Thr Ser Tyr Gly Thr
1505            1510              1515              1520

Thr Tyr Pro Tyr Ser Leu Met Arg
                1525

POLYNUCLEOTIDE ENCODING A RECEPTOR FOR A *BACILLUS THURINGIENSIS* TOXIN AND METHODS OF USE

This application is a divisional of U.S. Ser. No. 08/326,117, now U.S. Pat. No. 5,693,491.

ACKNOWLEDGEMENT OF GOVERNMENT SUPPORT

Work resulting in the present invention was supported in part by Research Agreement 58-319R-3-011 from the Office of International Cooperation and Development, U.S.D.A. and by Cooperative Agreement 58-5410-1-135 from the Arthropod-Borne Animal Disease Laboratory, Agricultural Research Service, U.S.D.A. and by Grant HD-18702 from the National Institutes of Health. The U.S. government has certain rights in this invention.

TECHNICAL FIELD

The invention relates to receptors that bind toxins from *Bacillus thuringiensis* and thus to pesticides and pest resistance. More particularly, the invention concerns recombinantly produced receptors that bind BT toxin and to their use in assays for improved pesticides, as well as in mediation of cell and tissue destruction, dissociation, dispersion, cell-to-cell association, and changes in morphology.

BACKGROUND ART

It has long been recognized that the bacterium *Bacillus thuringiensis* (BT) produces bacteriocidal proteins that are toxic to a limited range of insects, mostly in the orders Lepidoptera, Coleoptera and Diptera. Advantage has been taken of these toxins in controlling pests, mostly by applying bacteria to plants or transforming plants themselves so that they generate the toxins by virtue of their transgenic character. The toxins themselves are glycoprotein products of the cry gene as described by Höfte, H. et al. *Microbiol Rev* (1989) 5:242. It has been established that the toxins function in the brush border of the insect midgut epithelial cells as described by Gill, S. S. et al. *Annu Rev Entomol* (1992) 37:615. Specific binding of BT toxins to midgut brush border membrane vesicles has been reported by Hofmann, C. et al. *Proc Natl Acad Sci USA* (1988) 85:7844; Van Rie, J. et al. *Eur J Biochem* (1989) 186:239; and Van Rie, J. et al. *Appl Environ Microbiol* (1990) 56:1378.

Presumably, the toxins generated by BT exert their effects by some kind of interaction with receptors in the midgut. The purification of a particular receptor from *Manduca sexta* was reported by the present inventors in an article by Vadlamudi, R. K. et al. *J Biol Chem* (1993) 268:12334. In this report, the receptor protein was isolated by immuno-precipitating toxin-binding protein complexes with toxin-specific antisera and separating the complexes by SDS-PAGE followed by electroelution. However, to date, there has been no structural information concerning any insect receptor which binds BT toxin, nor have, to applicants' knowledge, any genes encoding these receptors been recovered.

DISCLOSURE OF THE INVENTION

The invention provides recombinant materials for the production of BT toxin-binding receptors as well as methods to employ these materials to generate receptors for use in screening assays for candidate pesticides. Since the native cDNA sequence encoding this receptor, designated BT-$R_1$, has been retrieved from the tobacco hornworm, encoding DNA for receptors in other species of insects, as well as in other organisms, which have homology to hornworm receptor can be obtained.

Thus, in one aspect, the invention is directed to a polynucleotide in purified and isolated form which comprises a nucleotide sequence encoding a receptor that binds a BT toxin and other ligands and which has the requisite homology to the BT-$R_1$ protein.

In other aspects, the invention is directed to expression systems for nucleotide sequences encoding the receptor, to methods of producing the receptor recombinantly, to the receptor as thus produced, to antibodies specifically immunoreactive with the receptor, to assay methods useful for screening candidate pesticides, to antisense polynucleotides corresponding to the coding sequence, to methods of targeting tissues and/or cells using the binding characteristics of the receptor, and to methods of manipulating tissues and/or cells using the function of the receptor.

BRIEF DESCRIPTION OF THE DRAWINGS

FIGS. 1A–1N (SEQ ID NO:1 and SEQ ID NO:2) show the nucleotide sequence and deduced amino acid sequence of cDNA encoding the BT-$R_1$ protein from *M. sexta*.

FIGS. 2A–2F (SEQ ID NO:2) show the cadherin motifs in the amino acid sequence of the BT-$R_1$ protien *M. sexta*.

MODES OF CARRYING OUT THE INVENTION

The invention provides, for the first time, sequence information concerning receptors that bind BT toxins in insect midguts.

The BT-$R_1$ cDNA clone retrieved as described in the examples below encodes a protein having an identical amino acid composition with that described for the native receptor. Furthermore, toxin-binding specificity and immunoreactivity are similar. The native 210 kD BT-$R_1$ specifically recognizes cryIA(b) toxin of BT-berliner; a $K_d$ value of 708 pM was obtained for the native protein.

The cryIA(b) toxin selectively kills *M. sexta* larvae with an $LC_{50}$ of 7.5 ng/cm$^2$ of diet surface. BT-$R_1$ binds the toxin under both reducing and nonreducing conditions and protease treatment of intestinal BBMV vesicles prepared from *M. sexta* showed that a 50 kD fragment of the 210 kD receptor is sufficient for toxin binding. The 50 kD toxin-binding domain is extracellular since the intestinal BBMV vesicles are oriented predominantly right side out as reported by Haase, W. H. et al. *Biochem J* (1978) 172:57. This is consistent with the characteristics of the deduced amino acid sequence of the cDNA clone described below, as well as with the binding of toxin to the surface of intact BT-$R_1$ transfected human embryonic 293 cells as described in Example 3.

Whereas a particular cDNA clone from the tobacco hornworm has been described as illustration, the availability of this sequence information permits retrieval of corresponding receptors responsive to BT and related toxins from other species. This is conveniently accomplished by using the cDNA obtained in the present invention as a probe for screening cDNA or genomic libraries under conditions of stringency which eliminate false positives and retrieve substantially only corresponding receptors with coding sequences that are homologous to the coding sequence for the receptor of the present invention. Thus, the BT-$R_1$ protein itself and receptor proteins encoded by a nucleotide sequence homologous to the native nucleotide sequence encoding BT-R$_1$ are provided by the invention. Alternatively, PCR-mediated cloning can be used; however, this method does not take advantage of the detailed and complete information that resides in the availability of the nucleotide sequence encoding the full-length receptor from M. sexta. Also, PCR-mediated cloning introduces errors in natural DNA sequences. Thus, by using the full-length cDNA as a probe under conditions of appropriate stringency, only nucleotide sequences encoding the corresponding receptors will be obtained. The standard hybridization conditions include hybridization with nonspecific DNA such as salmon DNA at 50° C. and washing at 45° C. To obtain corresponding receptors having the lowest detectable homology with the receptor from M. sexta, the cDNA probe is hybridized under conditions of low standard stringency (30–37° C. and 4–6×SSC). More closely related corresponding receptors are obtained by hybridizing the cDNA probe under moderate standard stringency conditions (40–50° C. in 1×SSC). A clone containing the cDNA insert for use as a probe was deposited at the American Type Culture Collection as ATCC 98713.

The distribution of receptors of appropriate homology in the animal kingdom is believed to be fairly wide. Indeed, it is thought that higher organisms such as mammals, including primates, contain corresponding receptors which are homologous to BT-R$_1$ but respond to modified forms of BT toxins. In addition, other parasites such as nematodes, both those that afflict plants and those that afflict animals, will contain corresponding receptors.

Although one of the advantages of the use of BT toxins as insecticides is its specificity for certain orders of insects, this specificity is believed to result from the particular structure of the BT toxin rather than the unavailability of a corresponding mechanism in other insect orders. Thus, modified forms of BT toxin would be effective with respect to insects which contain homologous but slightly different forms of the receptor from that of the BT-R$_1$ protein illustrated below.

As used herein, "A receptor that specifically binds a BT toxin" refers to a receptor which is homologous to the BT-R$_1$ protein illustrated herein and which binds to either BT toxins themselves or to BT toxins that are sufficiently modified so as to bind these receptors which provide the required homology to BT-R$_1$.

The criteria for inclusion of a receptor in the present invention are the requirements that 1) it behave as a receptor—i.e., be capable of being displayed at the cell membrane; 2) it be sufficiently homologous to the BT-R$_1$ receptor described herein that a nucleotide sequence encoding the protein hybridizes under the stringency conditions described above to the nucleotide sequence encoding BT-R$_1$ as contained in the plasmid deposited at the American Type Culture Collection as ATCC 98713; and 3) when displayed on the surface of a cell, it is capable of binding a BT toxin or a modified form of BT toxin that exerts a cytotoxic effect either on the cell in which the receptor resides or in a tissue with which the cell is associated.

The structural characteristics of the "modified BT toxin" are defined by the functional property set forth above, but it may be convenient to design modified forms of BT toxin by conservative amino acid substitutions or other known protein-manipulating techniques applied to naturally occurring BT toxins.

The presence of similar receptors in noninsect organisms as well as other insects besides those harboring BT-R$_1$ is supported by the sequence similarity of the BT-R$_1$ protein to that of the various members of the cadherin superfamily of proteins, which are membrane glycoproteins believed to mediate calcium-dependent cell aggregation and sorting. See, for example, Takeichi, M. Science (1991) 251:1451; and Takeichi, M. N Rev Biochem (1990) 59:237.

Included in this superfamily are desmoglien, desmocollins, the Drosophila fat tumor suppressor, human intestinal peptide transport protein and T-cadherin. All of these proteins share common extracellular motifs although their cytoplasmic domains differ. Goodwin, L. et al. Biochem Biophys Res Commun (1990) 173:1224; Holton, J. L. et al. J Cell Sci (1990) 97:239; Bestal, D. J. J Cell Biol (1992) 119:451; Mahoney, P. A. et al. Cell (1991) 853; Dantzig, A. H. et al. Science (1994) 264:430; and Sano, K. et al. EMBO J (1993) 12:2249. Inclusion of BT-R$_1$ in the cadherin superfamily is further supported by the report that EDTA decreases the binding of cryIA(b) toxin of BT to the 210 kD receptor of M. sexta (Martinez-Ramirez, A. C. et al. Biochm Biophys Res Commun (1994) 201:782).

It is noted below that the amino acid sequence of BT-R$_1$ reveals that a calcium-binding motif is present. This is consistent with the possibility that cells having receptors to bind toxin may themselves survive although they render the tissues in which they are included permeable to solutes and thus effect disintegration of the tissue. Such a mechanism is proposed for the death of insects that ingest the toxin via the epithelial cells in their midgut by Knowles, B. H. et al. Biochim Biophys Acta (1987) 924:509. Such a mechanism is also supported in part by the results set forth in Example 4 hereinbelow which indicate that the effect of the toxin on embryonic 293 cells modified to express the receptor at their surface is reversible.

Thus, in summary, the invention provides a family of receptors that is able to mediate the negative effects exerted by BT toxin or its modified forms on the cells expressing the receptor, by damaging the cells themselves and/or the tissue or organ of which the cells form a part. The receptor may be expressed natively at the surface of the target cells or the target cells may be modified to contain an expression system which will effect the display of receptor at the surface. The availability of this family of receptors and recombinant methods for its production and for the production of cells displaying it at their surfaces provides a number of opportunities to conduct screening assays for improved toxins, particularly insecticidal toxins, for generation of antibodies that can be useful as alternatives to chemotherapeutic agents for the destruction and/or dissociation of unwanted cells or tissues, and for the design of improved toxins and pharmaceuticals.

Screening Assays

The availability of the recombinant family of receptors of the present invention permits design of straightforward screening assays for toxins which will interact successfully with these receptors resulting in measurable effects on the cells in which the receptors reside. Briefly, suitable host cells, such as COS cells for transient expression, CHO cells for stable expression, and a variety of other mammalian and insect host cells can be modified to contain expression vectors appropriate to the hosts for the production of the receptors of the invention displayed on the surfaces of the cells. Since the receptors are natively membrane proteins, no particular design of the expression system is required in order to effect their disposition at the cell surface. Expression vectors suitable for any desired host are generally known in the art. For example, for mammalian expression, suitable control sequences include the SV40 and adenovirus promoters as constitutive promoters, the metallothionein inducible promoter, suitable enhancers, if desired, and termination signals and the like. For insect cells, the bacculovirus system is preferred. For other eucaryotic cells such as yeast, the glycolytic enzyme promoters and various amino acid synthesis promoters are commonly employed. Procaryotic cells such as E. coli also may be adapted for expression of the receptor in the assay of the invention, for instance by using a reporter gene under the control of cyclic AMP and operably linked to the receptor via protein G such that toxin binding will interrupt adenyl cyclase activity and thereby produce a detectable change in reporter gene activity. The assay system in a prokaryotic host may require further modification to compensate for lack of glycosylation which is known to occur in insect cells where the $BT\text{-}R_1$ protein is naturally expressed.

The cells are modified by transfection, retroviral infection, electroporation or other known means, to contain the desired expression system and then cultured under conditions wherein the receptor protein is produced and displayed. If desired, the cells are then recovered from the culture for use in the assay, or the culture itself can be used per se.

In the assays, the modified cells are contacted with the candidate toxin and the effect on metabolism or morphology is noted in the presence and absence of the candidate. The effect may be cytotoxic—i.e., the cells may themselves exhibit one of the indices of cell death, such as reduced thymidine uptake, slower increase in optical density of the culture, reduced exclusion of vital dyes (e.g., trypan blue), increased release of viability markers such as chromium and rubidium, and the like. The differential response between the toxin-treated cells and the cells absent the toxin is then noted. The strength of the toxin can be assessed by noting the strength of the response.

These assays may be conducted directly as described above or competitively with known toxins. For example, one approach might be to measure the diminution in binding of labeled BT cry toxin in the presence and absence of the toxin candidate.

In addition to simply screening candidates, the screen can be used to devise improved forms of toxins which are more specific or less specific to particular classes of insects as desired. The ability to determine binding affinity ($K_a$ and $K_d$), dissociation and association rates, and cytotoxic effects of a candidate allows quick, accurate and reproducible screening techniques for a large number of toxins and other ligands under identical conditions which was not possible heretofore. Such information will facilitate the selection of the most effective toxins and ligands for any given receptor obtained from any desired host cell.

Competition assays may also employ antibodies that are specifically immunoreactive with the receptor. Such antibodies can be prepared in the conventional manner by administering the purified receptor to a vertebrate animal, monitoring antibody titers and recovering the antisera or the antibody-producing cells for immortalization, to obtain immortalized cells capable of secreting antibodies of the appropriate specificity. Techniques for obtaining immortalized B cells and for screening them for secretion of the desired antibody are now conventional in the art. The resulting monoclonal antibodies may be more effective than the polyclonal antisera as competition reagents; furthermore, the availability of the immortalized cell line secreting the desired antibody assures uniformity of production of the same reagent over time. The information and the structural characteristics of toxins and ligands tested will permit a rational approach to designing more efficient toxins and ligands. Additionally, such assays will lead to a better understanding of the function and the structure/function relationship of both toxin/ligand and $BT\text{-}R_1$ analogs. In turn, this will allow the development of highly effective toxins/ligands. Ligands include natural and modified toxins, antibodies (anti-receptor and antiidiotypic antibodies which mimic a portion of a toxin that binds to a receptor, and whatever small molecules bind the receptors.

Therapeutic Strategies

Advantage may be taken of the ability of receptors to mediate the destruction, dissociation or association of cells, tissues or organs by utilizing the screening assay as a method to identify successful therapeutics in the treatment of, for example, malignancies, metastases and infectious microorganisms which naturally express receptors corresponding to $BT\text{-}R_1$. The presence of receptors corresponding to the $BT\text{-}R_1$ receptor illustrated herein and members of the family of receptors included in the invention in the undesired cells may be exploited by first assessing the interaction of a proposed therapeutic with the receptors on these cells in culture and then identifying agents which successfully interact with the receptors as useful candidate reagents. Antibodies reactive with these receptors comprise a class of promising therapeutic candidates.

In some applications target cells, tissues, organs, and microorganisms which do not express an effective receptor corresponding to the $BT\text{-}R_1$ receptor may be transformed or transfected to express an effective corresponding receptor. These targets then will be killed or manipulated with toxin or other ligands. For instance, yeast cells to be used for toxin assays for a particular insect may be transformed with a genetic construct for expression of the receptor from that insect which corresponds to the $BT\text{-}R_1$ receptor.

In another aspect of the invention the receptors corresponding to $BT\text{-}R_1$ in certain target cells may be manipulated by modified toxin or other ligands to prevent the normal response to toxin (dissociation, damage and death of membranes, cell, tissues and organisms). For instance, a ligand which binds to a corresponding receptor in such a way that normal receptor function is inhibited would thereby prevent the receptor from initiating the usual destructive effects in the presence of a normal ligand such as a toxin. In other words, the invention enables development of competitive inhibitors of a toxin or other ligand which normally initiates destructive or other effects via a receptor corresponding to $BT\text{-}R_1$.

The following examples are intended to illustrate but not to limit the invention.

EXAMPLE 1

Purification and Sequence Determination of $BT\text{-}R_1$ Protein

Midguts of M. sexta were extracted and the $BT\text{-}R_1$ protein purified according to the method of Vadlamudi, R. K. et al. J Biol Chem (1993) 268:1233, referenced above and incorporated herein by reference. The electroeluted band was confirmed to contain $BT\text{-}R_1$ protein by binding to $^{125}$I-cryIA (b) toxin. In gel electrophoresis, the protein bound to toxin had an apparent weight of approximately 210 kD under reducing and nonreducing conditions.

The purified electroeluted $BT\text{-}R_1$ was subjected to cyanogen bromide digestion and the cyanogen bromide fragments separated on a 17% high-resolution tricine SDS-polyacrylamide gel as described by Schagger, H. et al. Anal Biochem (1987) 166:368. The separated fragments were transferred to Problott membranes (Applied Biosystems)

and five bands were extracted and subjected to microsequencing using standard instrumentation. The amino acid sequences obtained were:

1. (Met)-Leu-Asp-Tyr-Glu-Val-Pro-Glu-Phe-Gln-Ser-Ile-Thr-Ile-Arg-Val-Val-Ala-Thr-Asp-Asn-Asn-Asp-Thr-Arg-His-Val-Gly-Val-Ala (SEQ ID NO:18);
2. (Met)-X-Glu-Thr-Tyr-Glu-Leu-Ile-Ile-His-Pro-Phe-Asn-Tyr-Tyr-Ala (SEQ ID NO:19);
3. (Met)-X-X-X-His-Gln-Leu-Pro-Leu-Ala-Gln-Asp-Ile-Lys-Asn-His (SEQ ID NO:20);
4. (Met)-Phe/Pro-Asn/Ile-Val-Arg/Tyr-Val-Asp-Ile/Gly (SEQ ID NO:21);
5. (Met)-Asn-Phe-Phe/His-Ser-Val-Asn-Arg/Asp-Glu (SEQ ID NO:22).

EXAMPLE 2

Recovery of cDNA

An *M. sexta* cDNA library was constructed from midgut tissue in λgt10 using the Superscript Choice System according to the manufacturer's instructions (Life Technologies, Inc.). Degenerate oligonucleotide probes were constructed based on the peptide sequences determined in Example 1 using the methods and approach described in Zhang, S. et al. *Gene* (1991) 105:61. Synthetic oligonucleotides corresponding to peptides 1–3 of Example 1 were labeled with $\gamma^{32}P$ using polynucleotide kinase and used as probes as described in the standard cloning manual of Maniatis, T. et al. *Molecular Cloning: A Laboratory Manual* (Cold Spring Harbor Laboratory, Cold Spring Harbor, N.Y., 2nd ed. 1989). A clone hybridizing to all three probes identified from 40 positive clones as hybridizing to all three of the probes was plaque-purified from a screen of $4 \times 10^5$ recombinants and subcloned into pBluescript (Stratagene). It contained an insert of 5571 bp.

Figure 1C:
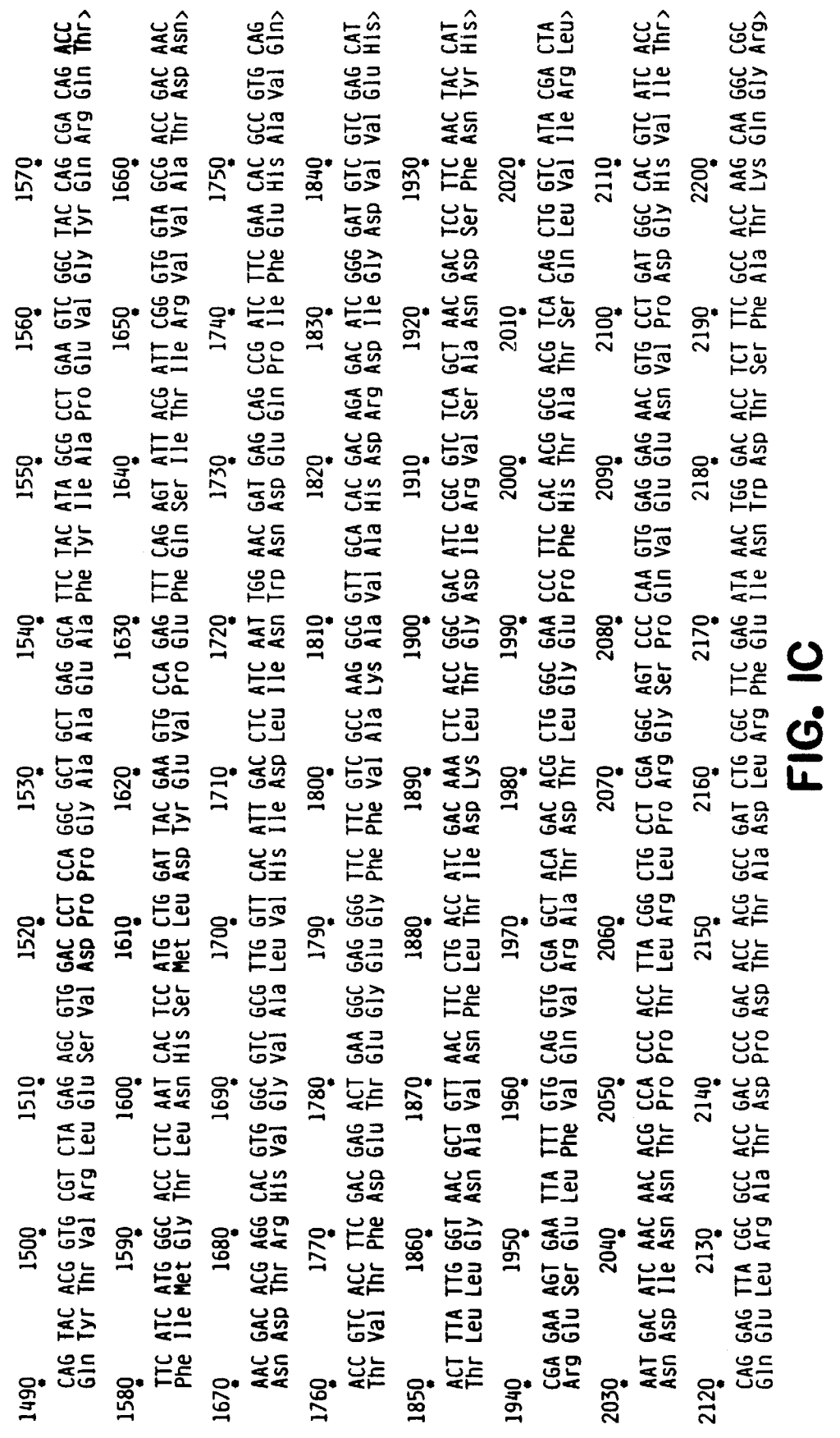
Figure 1G:
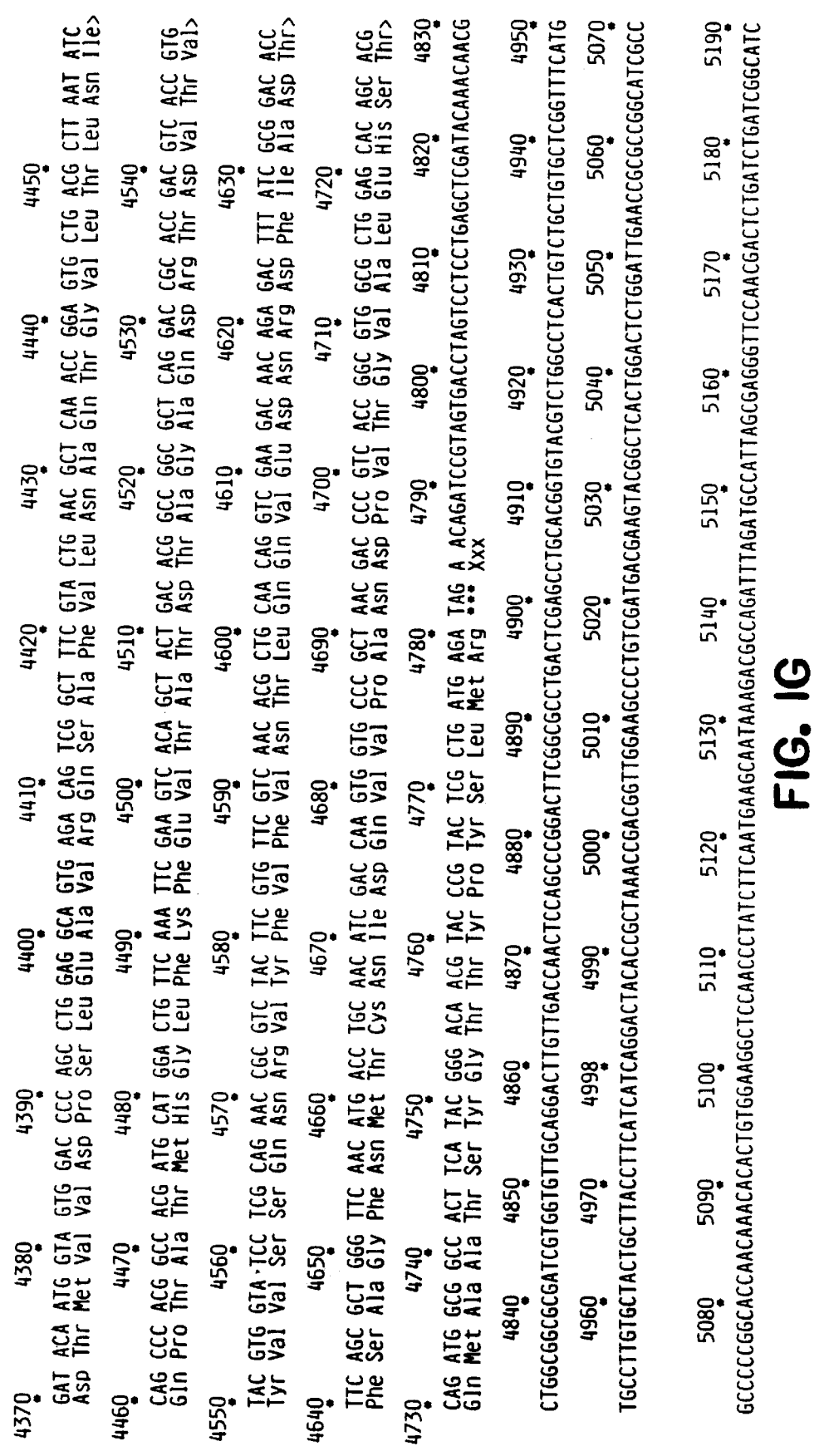

Double-stranded cDNA in pBluescript was sequenced in both directions by the dideoxy termination method with Sequanase (USB) according to the manufacturer's instructions. The sequencing showed an open reading frame of 4584 base pairs or 1528 amino acids along with a polyadenylation signal at position 5561. The sequence obtained and the deduced amino acid sequence is shown in FIGS. 1A–1H.

Thus, the deduced protein has a molecular mass of 172 kD and a pI of approximately 4.5. The amino acid sequences of the cyanogen bromide fragments of native receptor match perfectly within the deduced amino acid sequence. The open reading frame begins with an ATG that is flanked by the consensus translation initiation sequence GAGATGG for eucaryotic mRNAs as described by Kozak, M. *Nucleic Acids Res* (1987) 15:8125.

As shown in FIGS. 1A–1H, the deduced amino acid sequence includes a putative signal, shown underlined, preceding the mature N-terminus Asn-Glu-Arg-etc. Eleven repeats are shown in the extracellular region upstream of the membrane domain, shown with the heavy underline, at positions 1406–1427. The end of the 11th repeat is shown with an arrowhead. The positions of the five CNBR fragments are also shown under the complete sequence.

FIGS. 2A–2F compare the BT-R$_1$ sequence obtained herein with other members of the cadherin family. The other cadherins are mouse P cadherin (MP-EC1); Drosophila fat EC18 (fat EC-18) and protocadherin (PC42-EC-2), and human intestinal transporter (EC-11) (HPT-1-EC-1). Conserved residues are boxed.

To confirm that the sequenced clone encoded full-length BT-R$_1$ protein, total mRNA was prepared from midguts of *M. sexta* subjected to Northern blot by hybridization with the antisense 4.8 kb SacI fragment of the BT-R$_1$ cDNA clone. The Northern blot analysis was conducted by hybridizing to the antisense probe at 42° C. and 50% formamide, 5×Denhardt×s Reagent, 5×SSCP and 50 µg/ml salmon sperm DNA. The filter was then washed two times with 1×SSC+0.1% SDS and two times with 0.15×SSC+0.1% SDS at 42° C. Each wash was roughly 20 minutes. The filter was then exposed to X-ray film for 24 hours. The 4.8 kb probe hybridized to a single 5.6 kb band.

The BT-R$_1$ clone was translated using rabbit reticulolysate and the resulting translated products were immunoprecipitated with antisera raised against native protein encoded by BT-R$_1$. For the in vitro translation, pBluescript plasmid containing BT-R$_1$ cDNA was linearized and transcribed with T$_3$ polymerase (Pharmacia). The translation was conducted according to manufacturer's instructions with nuclease-treated rabbit reticulolysate (Life Technologies, Inc.). After one hour of incubation at 30° C., the reaction mixture was combined with an equal volume of SDS buffer or lysed with 50 mM Tris buffer containing 1% NP40 and 250 mM NaCl (pH 8.0) for immunoprecipitation. Preimmune serum was used as a control. Translation and immunoprecipitation products were electrophoresed on a 7.5% SDS-polyacrylamide gel fixed, treated with Enhance (Dupont NEN), dried and exposed to X-ray film for 12 hours.

Two protein bands of approximately 172 kD and 150 kD as determined by SDS-PAGE were obtained; it is postulated that the 150 kD translation product was due to initiation of translation from an internal methionine at amino acid 242. This is consistent with the observations of Kozak, M. *Mol Cell Biol* (1989) 9:5073.

Thus, both results confirm that a full-length clone was obtained.

EXAMPLE 3

Recombinant Production and Characteristics of the BT-R$_1$ Protein

The BT-R$_1$ cDNA clone was subcloned into the mammalian expression vector pcDNA3 (Invitrogen) and the construct transfected into COS-7 cells. Membranes isolated from the COS-7 transfectants were solubilized, electrophoresed and ligand blotted with $^{125}$I-cryIA(b) toxin. The cells were harvested 60 hours after transfection, washed with phosphate-buffered saline and lysed by freezing in liquid nitrogen. Cell membranes were prepared by differential centrifugation as described by Elshourbagy, N. A. et al. *J Biol Chem* (1993) 266:3873. Control cells were COS-7 cells transfected with pcDNA3.

The cell membranes (10 µg) were separated on 7.5% SDS-PAGE blotted to a nylon membrane and blocked with Tris-buffered saline containing 5% nonfat dry milk powder, 5% glycerol and 1% Tween-20. The nylon membrane was then incubated with $^{125}$I-cryIA(b) toxin ($2 \times 10^5$ cpm/ml) for two hours with blocking buffer, dried and exposed to X-ray film at −70° C. The labeled toxin bound to a 210±5 kD protein; the 210 kD band was observed only in lanes containing membranes prepared from either *M. sexta* or COS-7 cells transfected with the BT-R$_1$ cDNA construct containing 4810 bp of cDNA comprising the open reading frame.

The discrepancy between the 210 kD protein expressed and the calculated 172 kD molecular weight is due to glycosylation of the protein; in vitro translation of the cDNA clone, as described above, which does not result in glycosylation, does produce the 172 kD protein. To verify this, the COS-7 produced protein was subjected to digestion with N-glycosidase-F by first denaturing the purified protein by boiling in 1% SDS for 5 minutes followed by addition of NP-40 to a final concentration of 1% in the presence of 0.1% SDS, and then incubating the denatured protein in sodium phosphate buffer, pH 8.5 at 37° C. with N-glycosidase-F for 10 hours. Controls were incubated under the same conditions without enzyme. Digestion products were separated on a 7.5% SDS-PAGE and stained with Coomassie brilliant blue. This glycosidase treatment reduced the molecular weight of BT-$R_1$ protein from 210 to 190 kD; this indicates N-glycosylation at some of the 16 consensus N-glycosylation sites in the protein. Treatment of BT-$R_1$ with O-glycosidase and neuraminidase did not alter the mobility of the protein.

In addition, embryonic 293 cells were transfected with the BT-$R_1$ cDNA clone in pcDNA3 and incubated with the labeled toxin (0.32 nM) in the presence of increasing concentrations (0 to $10^{-6}$ M) of unlabeled toxin. Nonspecific binding was measured as bound radioactivity in the presence of 1 μM unlabeled toxin. A value for the dissociation constant ($K_d$) of 1015 pM was determined by Scatchard analysis; this is approximately the same value that was obtained for the natural receptor as described by Vadlamudi, R. K. et al. *J Biol Chem* (1993) (supra).

EXAMPLE 4

Physiological Effect of BT Toxin on Modified Embryonic 293 Cells

Both unmodified embryonic 293 cells, and 293 cells which have been modified to produce the BT-$R_1$ receptor as described in Example 3, when cultured in vitro form adherent star-shaped clusters. When BT toxin (200 nM) is added to serum-free medium, the clusters round up and release from the plastic surfaces of the culture dish. This effect is also observed under known conditions of cytotoxicity for 293 cells. The foregoing effect is observed only when the cells are cultured in serum-free medium since the toxin binds to serum and would thus be ineffective under conditions where serum is present.

However, in the presence of anti-receptor antisera, this effect of BT toxin is blocked. Also, when serum is added back to a culture of modified E293 cells which has been treated in serum-free conditions with the toxin, the cells revert to their normal star-shaped adherent cluster shapes. This indicates that the effect of the toxin is reversible.

I claim:

1. A purified and isolated polynucleotide which comprises a nucleotide sequence complementary to a nucleotide sequence encoding a receptor which specifically binds cryIA (b) toxin of BT-berliner wherein said receptor has the amino acid sequence shown in SEQ ID NO: 2, or wherein said receptor is encoded by a polynucleotide that hybridizes at 40–50° C. in 1×SSC, or equivalent conditions thereof, to a nucleotide having SEQ ID NO: 1.

2. A method to modify target cells so as to render them susceptible to interaction with a BT toxin which method comprises modifying said cells to contain a recombinant expression system that comprises a control sequences operable in said cells operably linked to a nucleotide sequence which encodes a receptor which specifically binds cryIA(b) toxin of BT-berliner, wherein said receptor has the amino acid sequence of the receptor shown in SEQ ID NO: 2, or wherein said receptor is a naturally occurring receptor that is encoded by a nucleotide sequence that hybridizes at 40–50° C. in 1×SSC, or equivalent conditions thereof, to a nucleotide having SEQ ID NO: 1; and culturing the cells under conditions wherein said receptor is disposed at the surface of the cells.

3. Cells modified by the method of claim 2.

4. A method to damage tissue which method comprises modifying target cells in said tissue by the method of claim 2 and contacting said tissue containing said target cells with an amount of BT toxin effective to interact with said receptor.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 5577 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 197..4780

(xi) SEQUENCE DESCRIPTION: SEQ ID NO:1:

```
GACCAATCGG AGTGTGGTGA ATTTTTGGAA AATATTTTGT GCGGTTCCTT TAGTTGTGTA      60

ATATAGTACT TTAGTTACAA ATTTGGAATA ATTTGGCAGC AAAACCATCT GCAGCAACAA     120

AATCATCTGC AGCTGCGAAA TCATCTGCAG CAGCAAAAGC ATCTTCAGGA GCGAGAAAAG     180

CCCCAAATAA TGTGAG ATG GCA GTT GAC GTC CGA ATC GCT GCC TTC CTG        229
                Met Ala Val Asp Val Arg Ile Ala Ala Phe Leu
                 1               5                  10

CTG GTG TTT ATA GCG CCT GCA GTT TTA GCT CAA GAG AGA TGT GGG TAT      277
Leu Val Phe Ile Ala Pro Ala Val Leu Ala Gln Glu Arg Cys Gly Tyr
             15                  20                  25

ATG ACC GCC ATC CCA AGG CTA CCA CGA CCG GAT AAT TTG CCA GTA CTA      325
Met Thr Ala Ile Pro Arg Leu Pro Arg Pro Asp Asn Leu Pro Val Leu
         30                  35                  40

AAT TTT GAA GGC CAG ACA TGG AGT CAG AGG CCC CTG CTC CCC GCC CCG      373
Asn Phe Glu Gly Gln Thr Trp Ser Gln Arg Pro Leu Leu Pro Ala Pro
     45                  50                  55

GAG CGG GAT GAC CTG TGC ATG GAC GCC TAC CAC GTG ATA ACA GCC AAC      421
Glu Arg Asp Asp Leu Cys Met Asp Ala Tyr His Val Ile Thr Ala Asn
 60                  65                  70                  75
```

-continued

| | |
|---|---|
| CTC GGC ACG CAG GTC ATC TAC ATG GAT GAA GAG ATA GAA GAC GAA ATC<br>Leu Gly Thr Gln Val Ile Tyr Met Asp Glu Glu Ile Glu Asp Glu Ile<br>                        80                                85                            90 | 469 |
| ACC ATC GCC ATA CTT AAT TAT AAC GGA CCA TCA ACT CCG TTC ATT GAA<br>Thr Ile Ala Ile Leu Asn Tyr Asn Gly Pro Ser Thr Pro Phe Ile Glu<br>                        95                                100                          105 | 517 |
| CTG CCA TTT TTA TCC GGT TCG TAC AAT CTG CTG ATG CCG GTC ATC AGG<br>Leu Pro Phe Leu Ser Gly Ser Tyr Asn Leu Leu Met Pro Val Ile Arg<br>                110                                115                          120 | 565 |
| AGA GTT GAC AAC GGG AGT GCA TCT CAT CAT CAC GCA AGA CAG CAT TAC<br>Arg Val Asp Asn Gly Ser Ala Ser His His His Ala Arg Gln His Tyr<br>    125                                130                              135 | 613 |
| GAG TTG CCC GGC ATG CAG CAG TAC ATG TTC AAT GTG CGC GTG GAC GGC<br>Glu Leu Pro Gly Met Gln Gln Tyr Met Phe Asn Val Arg Val Asp Gly<br>140                              145                              150                          155 | 661 |
| CAG TCG CTG GTG GCA GGC GTG TCT CTC GCT ATC GTC AAC ATA GAT GAC<br>Gln Ser Leu Val Ala Gly Val Ser Leu Ala Ile Val Asn Ile Asp Asp<br>                        160                              165                          170 | 709 |
| AAC GCG CCC ATC ATA CAA AAC TTC GAG CCT TGC CGG GTT CCT GAA CTG<br>Asn Ala Pro Ile Ile Gln Asn Phe Glu Pro Cys Arg Val Pro Glu Leu<br>            175                              180                          185 | 757 |
| GGC GAG CCA GGG TTG ACA GAA TGC ACA TAC CAA GTA TCG GAC GCG GAC<br>Gly Glu Pro Gly Leu Thr Glu Cys Thr Tyr Gln Val Ser Asp Ala Asp<br>                  190                              195                          200 | 805 |
| GGA CGG ATC AGC ACA GAG TTC ATG ACG TTC AGG ATC GAC AGC GTT CGT<br>Gly Arg Ile Ser Thr Glu Phe Met Thr Phe Arg Ile Asp Ser Val Arg<br>    205                                210                              215 | 853 |
| GGC GAC GAG GAG ACC TTC TAC ATC GAA CGG ACG AAT ATC CCC AAC CAA<br>Gly Asp Glu Glu Thr Phe Tyr Ile Glu Arg Thr Asn Ile Pro Asn Gln<br>220                              225                              230                          235 | 901 |
| TGG ATG TGG CTA AAT ATG ACC ATA GGC GTT AAT ACC TCG CTC AAC TTC<br>Trp Met Trp Leu Asn Met Thr Ile Gly Val Asn Thr Ser Leu Asn Phe<br>                    240                              245                          250 | 949 |
| GTC ACC AGT CCG CTG CAT ATA TTC AGC GTG ACA GCC CTG GAC TCG CTC<br>Val Thr Ser Pro Leu His Ile Phe Ser Val Thr Ala Leu Asp Ser Leu<br>              255                              260                          265 | 997 |
| CCG AAC ACC CAC ACG GTG ACT ATG ATG GTG CAA GTG GCG AAT GTG AAC<br>Pro Asn Thr His Thr Val Thr Met Met Val Gln Val Ala Asn Val Asn<br>        270                              275                            280 | 1045 |
| AGC CGT CCG CCG CGC TGG CTG GAG ATC TTC GCT GTC CAA CAG TTT GAA<br>Ser Arg Pro Pro Arg Trp Leu Glu Ile Phe Ala Val Gln Gln Phe Glu<br>285                              290                              295 | 1093 |
| GAG AAA TCT TAC CAA AAC TTC ACA GTG AGG GCG ATC GAC GGA GAC ACT<br>Glu Lys Ser Tyr Gln Asn Phe Thr Val Arg Ala Ile Asp Gly Asp Thr<br>300                              305                              310                          315 | 1141 |
| GAG ATC AAT ATG CCT ATC AAC TAC AGG CTG ATC ACA AAT GAG GAA GAC<br>Glu Ile Asn Met Pro Ile Asn Tyr Arg Leu Ile Thr Asn Glu Glu Asp<br>                    320                              325                          330 | 1189 |
| ACA TTC TTC AGC ATT GAG GCC CTG CCT GGT GGA AAA AGC GGG GCT GTA<br>Thr Phe Phe Ser Ile Glu Ala Leu Pro Gly Gly Lys Ser Gly Ala Val<br>              335                              340                          345 | 1237 |
| TTC CTC GTG TCG CCA ATT GAC CGC GAC ACA CTG CAA CGA GAG GTG TTT<br>Phe Leu Val Ser Pro Ile Asp Arg Asp Thr Leu Gln Arg Glu Val Phe<br>            350                            355                          360 | 1285 |
| CCA CTT ACG ATC GTC GCT TAC AAA TAT GAT GAG GAG GCC TTC TCC ACA<br>Pro Leu Thr Ile Val Ala Tyr Lys Tyr Asp Glu Glu Ala Phe Ser Thr<br>365                              370                              375 | 1333 |
| TCA ACA AAC GTG GTC ATC ATT GTG ACA GAC ATC AAC GAC CAA AGA CCT<br>Ser Thr Asn Val Val Ile Ile Val Thr Asp Ile Asn Asp Gln Arg Pro<br>380                              385                              390                          395 | 1381 |

```
GAA CCT ATA CAC AAG GAA TAT CGA CTG GCA ATC ATG GAG GAG ACG CCC        1429
Glu Pro Ile His Lys Glu Tyr Arg Leu Ala Ile Met Glu Glu Thr Pro
            400                 405                 410

CTG ACC CTC AAC TTC GAT AAA GAA TTC GGA TTT CAT GAT AAG GAT TTA        1477
Leu Thr Leu Asn Phe Asp Lys Glu Phe Gly Phe His Asp Lys Asp Leu
            415                 420                 425

GGT CAA AAC GCT CAG TAC ACG GTG CGT CTA GAG AGC GTG GAC CCT CCA        1525
Gly Gln Asn Ala Gln Tyr Thr Val Arg Leu Glu Ser Val Asp Pro Pro
            430                 435                 440

GGC GCT GCT GAG GCA TTC TAC ATA GCG CCT GAA GTC GGC TAC CAG CGA        1573
Gly Ala Ala Glu Ala Phe Tyr Ile Ala Pro Glu Val Gly Tyr Gln Arg
            445                 450                 455

CAG ACC TTC ATC ATG GGC ACC CTC AAT CAC TCC ATG CTG GAT TAC GAA        1621
Gln Thr Phe Ile Met Gly Thr Leu Asn His Ser Met Leu Asp Tyr Glu
460                 465                 470                 475

GTG CCA GAG TTT CAG AGT ATT ACG ATT CGG GTG GTA GCG ACC GAC AAC        1669
Val Pro Glu Phe Gln Ser Ile Thr Ile Arg Val Val Ala Thr Asp Asn
                480                 485                 490

AAC GAC ACG AGG CAC GTG GGC GTC GCG TTG GTT CAC ATT GAC CTC ATC        1717
Asn Asp Thr Arg His Val Gly Val Ala Leu Val His Ile Asp Leu Ile
            495                 500                 505

AAT TGG AAC GAT GAG CAG CCG ATC TTC GAA CAC GCC GTG CAG ACC GTC        1765
Asn Trp Asn Asp Glu Gln Pro Ile Phe Glu His Ala Val Gln Thr Val
            510                 515                 520

ACC TTC GAC GAG ACT GAA GGC GAG GGG TTC TTC GTC GCC AAG GCG GTT        1813
Thr Phe Asp Glu Thr Glu Gly Glu Gly Phe Phe Val Ala Lys Ala Val
            525                 530                 535

GCA CAC GAC AGA GAC ATC GGG GAT GTC GTC GAG CAT ACT TTA TTG GGT        1861
Ala His Asp Arg Asp Ile Gly Asp Val Val Glu His Thr Leu Leu Gly
540                 545                 550                 555

AAC GCT GTT AAC TTC CTG ACC ATC GAC AAA CTC ACC GGC GAC ATC CGC        1909
Asn Ala Val Asn Phe Leu Thr Ile Asp Lys Leu Thr Gly Asp Ile Arg
                560                 565                 570

GTC TCA GCT AAC GAC TCC TTC AAC TAC CAT CGA GAA AGT GAA TTA TTT        1957
Val Ser Ala Asn Asp Ser Phe Asn Tyr His Arg Glu Ser Glu Leu Phe
            575                 580                 585

GTG CAG GTG CGA GCT ACA GAC ACG CTG GGC GAA CCC TTC CAC ACG GCG        2005
Val Gln Val Arg Ala Thr Asp Thr Leu Gly Glu Pro Phe His Thr Ala
            590                 595                 600

ACG TCA CAG CTG GTC ATA CGA CTA AAT GAC ATC AAC AAC ACG CCA CCC        2053
Thr Ser Gln Leu Val Ile Arg Leu Asn Asp Ile Asn Asn Thr Pro Pro
605                 610                 615

ACC TTA CGG CTG CCT CGA GGC AGT CCC CAA GTG GAG GAG AAC GTG CCT        2101
Thr Leu Arg Leu Pro Arg Gly Ser Pro Gln Val Glu Glu Asn Val Pro
620                 625                 630                 635

GAT GGC CAC GTC ATC ACC CAG GAG TTA CGC GCC ACC GAC CCC GAC ACC        2149
Asp Gly His Val Ile Thr Gln Glu Leu Arg Ala Thr Asp Pro Asp Thr
                640                 645                 650

ACG GCC GAT CTG CGC TTC GAG ATA AAC TGG GAC ACC TCT TTC GCC ACC        2197
Thr Ala Asp Leu Arg Phe Glu Ile Asn Trp Asp Thr Ser Phe Ala Thr
            655                 660                 665

AAG CAA GGC CGC CAG GCT AAC CCC GAC GAG TTT AGG AAT TGC GTG GAA        2245
Lys Gln Gly Arg Gln Ala Asn Pro Asp Glu Phe Arg Asn Cys Val Glu
            670                 675                 680

ATC GAG ACC ATC TTC CCC GAG ATT AAC AAC CGG GGA CTG GCT ATC GGC        2293
Ile Glu Thr Ile Phe Pro Glu Ile Asn Asn Arg Gly Leu Ala Ile Gly
            685                 690                 695

CGC GTT GTA GCG CGC GAA ATC AGA CAC AAC GTG ACC ATA GAC TAC GAG        2341
Arg Val Val Ala Arg Glu Ile Arg His Asn Val Thr Ile Asp Tyr Glu
700                 705                 710                 715
```

```
GAG TTT GAG GTC CTC TCC CTC ACA GTG AGG GTG CGT GAC CTT AAC ACC      2389
Glu Phe Glu Val Leu Ser Leu Thr Val Arg Val Arg Asp Leu Asn Thr
                    720                 725                 730

GTC TAC GGA GAC GAC TAC GAC GAA TCG ATG CTC ACA ATA ACT ATA ATC      2437
Val Tyr Gly Asp Asp Tyr Asp Glu Ser Met Leu Thr Ile Thr Ile Ile
                    735                 740                 745

GAT ATG AAC GAC AAC GCG CCG GTG TGG GTG GAG GGG ACT CTG GAG CAG      2485
Asp Met Asn Asp Asn Ala Pro Val Trp Val Glu Gly Thr Leu Glu Gln
                    750                 755                 760

AAC TTC CGA GTC CGC GAG ATG TCG GCG GGC GGG CTC GTG GTG GGC TCC      2533
Asn Phe Arg Val Arg Glu Met Ser Ala Gly Gly Leu Val Val Gly Ser
            765                 770                 775

GTG CGC GCG GAC GAC ATC GAC GGA CCG CTC TAC AAC CAA GTG CGA TAC      2581
Val Arg Ala Asp Asp Ile Asp Gly Pro Leu Tyr Asn Gln Val Arg Tyr
780                 785                 790                 795

ACC ATT TTC CCT CGT GAA GAC ACA GAT AAG GAC CTG ATA ATG ATC GAC      2629
Thr Ile Phe Pro Arg Glu Asp Thr Asp Lys Asp Leu Ile Met Ile Asp
                    800                 805                 810

TTC CTC ACG GGT CAA ATT TCC GTG AAC ACA AGC GGC GCC ATC GAC GCG      2677
Phe Leu Thr Gly Gln Ile Ser Val Asn Thr Ser Gly Ala Ile Asp Ala
                    815                 820                 825

GAT ACT CCT CCA CGC TTC CAC CTC TAC TAT ACA GTG GTC GCT AGT GAC      2725
Asp Thr Pro Pro Arg Phe His Leu Tyr Tyr Thr Val Val Ala Ser Asp
                830                 835                 840

CGA TGC TCG ACA GAA GAT CCT GCA GAT TGC CCC CCT GAC CCG ACT TAT      2773
Arg Cys Ser Thr Glu Asp Pro Ala Asp Cys Pro Pro Asp Pro Thr Tyr
            845                 850                 855

TGG GAA ACC GAA GGA AAT ATC ACA ATC CAC ATC ACC GAC ACG AAC AAC      2821
Trp Glu Thr Glu Gly Asn Ile Thr Ile His Ile Thr Asp Thr Asn Asn
860                 865                 870                 875

AAG GTC CCG CAG GCG GAA ACG ACT AAG TTC GAT ACC GTC GTG TAT ATT      2869
Lys Val Pro Gln Ala Glu Thr Thr Lys Phe Asp Thr Val Val Tyr Ile
                    880                 885                 890

TAC GAG AAC GCA ACC CAC TTA GAC GAG GTG GTC ACT CTG ATA GCC AGT      2917
Tyr Glu Asn Ala Thr His Leu Asp Glu Val Val Thr Leu Ile Ala Ser
                    895                 900                 905

GAT CTT GAC AGA GAC GAA ATA TAC CAC ACG GTG AGC TAC GTC ATC AAT      2965
Asp Leu Asp Arg Asp Glu Ile Tyr His Thr Val Ser Tyr Val Ile Asn
            910                 915                 920

TAT GCA GTG AAC CCT CGA CTG ATG AAC TTC TTC TCC GTG AAC CGA GAG      3013
Tyr Ala Val Asn Pro Arg Leu Met Asn Phe Phe Ser Val Asn Arg Glu
            925                 930                 935

ACC GGC CTG GTG TAC GTG GAC TAT GAG ACC CAG GGT AGT GGC GAG GTG      3061
Thr Gly Leu Val Tyr Val Asp Tyr Glu Thr Gln Gly Ser Gly Glu Val
940                 945                 950                 955

CTG GAC CGT GAT GGT GAT GAA CCA ACG CAC CGT ATC TTC TTC AAC CTC      3109
Leu Asp Arg Asp Gly Asp Glu Pro Thr His Arg Ile Phe Phe Asn Leu
                960                 965                 970

ATC GAC AAC TTC ATG GGG GAA GGA GAA GGT AAC AGA AAT CAG AAC GAC      3157
Ile Asp Asn Phe Met Gly Glu Gly Glu Gly Asn Arg Asn Gln Asn Asp
                    975                 980                 985

ACA GAA GTT CTC GTT ATC TTG TTG GAT GTG AAT GAC AAT GCT CCT GAA      3205
Thr Glu Val Leu Val Ile Leu Leu Asp Val Asn Asp Asn Ala Pro Glu
                    990                 995                 1000

TTG CCA CCG CCG AGC GAA CTC TCT TGG ACT ATA TCT GAG AAC CTT AAG      3253
Leu Pro Pro Pro Ser Glu Leu Ser Trp Thr Ile Ser Glu Asn Leu Lys
            1005                1010                1015

CAG GGC GTC CGT CTT GAA CCA CAT ATC TTC GCC CCG GAC CGC GAC GAG      3301
Gln Gly Val Arg Leu Glu Pro His Ile Phe Ala Pro Asp Arg Asp Glu
1020                1025                1030                1035
```

-continued

```
CCC GAC ACA GAC AAC TCC AGG GTC GGC TAC GAG ATC CTG AAC CTC AGC        3349
Pro Asp Thr Asp Asn Ser Arg Val Gly Tyr Glu Ile Leu Asn Leu Ser
            1040                1045                1050

ACG GAG CGG GAC ATC GAA GTG CCG GAG CTG TTT GTG ATG ATA CAG ATC        3397
Thr Glu Arg Asp Ile Glu Val Pro Glu Leu Phe Val Met Ile Gln Ile
            1055                1060                1065

GCG AAC GTC ACG GGA GAG CTG GAG ACC GCC ATG GAC CTC AAG GGA TAT        3445
Ala Asn Val Thr Gly Glu Leu Glu Thr Ala Met Asp Leu Lys Gly Tyr
            1070                1075                1080

TGG GGG ACG TAC GCT ATA CAT ATA CGG GCA TTC GAC CAC GGC ATT CCG        3493
Trp Gly Thr Tyr Ala Ile His Ile Arg Ala Phe Asp His Gly Ile Pro
            1085                1090                1095

CAA ATG TCC ATG AAC GAG ACA TAT GAG CTG ATC ATC CAT CCG TTC AAC        3541
Gln Met Ser Met Asn Glu Thr Tyr Glu Leu Ile Ile His Pro Phe Asn
1100                1105                1110                1115

TAC TAC GCG CCT GAG TTC GTC TTC CCG ACC AAC GAT GCC GTC ATA CGA        3589
Tyr Tyr Ala Pro Glu Phe Val Phe Pro Thr Asn Asp Ala Val Ile Arg
            1120                1125                1130

CTT GCG AGG GAA CGA GCT GTA ATC AAT GGA GTT CTA GCG ACA GTG AAC        3637
Leu Ala Arg Glu Arg Ala Val Ile Asn Gly Val Leu Ala Thr Val Asn
            1135                1140                1145

GGA GAG TTC TTG GAG CGG ATA TCG GCG ACT GAT CCG GAC GGA CTC CAC        3685
Gly Glu Phe Leu Glu Arg Ile Ser Ala Thr Asp Pro Asp Gly Leu His
            1150                1155                1160

GCG GGC GTC GTC ACC TTC CAA GTG GTA GGC GAT GAG GAA TCA CAA CGG        3733
Ala Gly Val Val Thr Phe Gln Val Val Gly Asp Glu Glu Ser Gln Arg
            1165                1170                1175

TAC TTT CAA GTA GTT AAC GAT GGC GAG AAC CTC GGC TCG TTG AGG TTA        3781
Tyr Phe Gln Val Val Asn Asp Gly Glu Asn Leu Gly Ser Leu Arg Leu
1180                1185                1190                1195

CTG CAA GCC GTT CCA GAG GAG ATC AGG GAG TTC CGG ATA ACG ATT CGC        3829
Leu Gln Ala Val Pro Glu Glu Ile Arg Glu Phe Arg Ile Thr Ile Arg
            1200                1205                1210

GCT ACA GAC CAG GGA ACG GAC CCA GGA CCG CTG TCC ACG GAC ATG ACG        3877
Ala Thr Asp Gln Gly Thr Asp Pro Gly Pro Leu Ser Thr Asp Met Thr
            1215                1220                1225

TTC AGA GTT GTT TTT GTG CCC ACG CAA GGA GAA CCT AGA TTC GCG TCC        3925
Phe Arg Val Val Phe Val Pro Thr Gln Gly Glu Pro Arg Phe Ala Ser
            1230                1235                1240

TCA GAA CAT GCT GTC GCT TTC ATA GAA AAG AGT GCC GGC ATG GAA GAG        3973
Ser Glu His Ala Val Ala Phe Ile Glu Lys Ser Ala Gly Met Glu Glu
            1245                1250                1255

TCT CAC CAA CTT CCT CTA GCA CAA GAC ATC AAG AAC CAT CTC TGT GAA        4021
Ser His Gln Leu Pro Leu Ala Gln Asp Ile Lys Asn His Leu Cys Glu
1260                1265                1270                1275

GAC GAC TGT CAC AGC ATT TAC TAT CGT ATT ATC GAT GGC AAC AGC GAA        4069
Asp Asp Cys His Ser Ile Tyr Tyr Arg Ile Ile Asp Gly Asn Ser Glu
            1280                1285                1290

GGT CAT TTC GGC CTG GAT CCT GTT CGC AAC AGG TTG TTC CTG AAG AAA        4117
Gly His Phe Gly Leu Asp Pro Val Arg Asn Arg Leu Phe Leu Lys Lys
            1295                1300                1305

GAG CTG ATA AGG GAA CAA AGT GCC TCC CAC ACT CTG CAA GTG GCG GCT        4165
Glu Leu Ile Arg Glu Gln Ser Ala Ser His Thr Leu Gln Val Ala Ala
            1310                1315                1320

AGT AAC TCG CCC GAT GGT GGC ATT CCA CTT CCT GCT TCC ATC CTT ACT        4213
Ser Asn Ser Pro Asp Gly Gly Ile Pro Leu Pro Ala Ser Ile Leu Thr
            1325                1330                1335

GTC ACT GTT ACC GTG AGG GAG GCA GAC CCT CGT CCA GTG TTT GTG AGG        4261
Val Thr Val Thr Val Arg Glu Ala Asp Pro Arg Pro Val Phe Val Arg
            1340                1345                1350                1355
```

```
GAA TTG TAC ACC GCA GGG ATA TCC ACA GCG GAC TCC ATC GGC AGA GAG       4309
Glu Leu Tyr Thr Ala Gly Ile Ser Thr Ala Asp Ser Ile Gly Arg Glu
            1360                1365                1370

CTC CTC AGA TTA CAT GCG ACC CAG TCT GAA GGC TCG GCC ATT ACT TAT       4357
Leu Leu Arg Leu His Ala Thr Gln Ser Glu Gly Ser Ala Ile Thr Tyr
        1375                1380                1385

GCT ATA GAC TAC GAT ACA ATG GTA GTG GAC CCC AGC CTG GAG GCA GTG       4405
Ala Ile Asp Tyr Asp Thr Met Val Val Asp Pro Ser Leu Glu Ala Val
        1390                1395                1400

AGA CAG TCG GCT TTC GTA CTG AAC GCT CAA ACC GGA GTG CTG ACG CTT       4453
Arg Gln Ser Ala Phe Val Leu Asn Ala Gln Thr Gly Val Leu Thr Leu
        1405                1410                1415

AAT ATC CAG CCC ACG GCC ACG ATG CAT GGA CTG TTC AAA TTC GAA GTC       4501
Asn Ile Gln Pro Thr Ala Thr Met His Gly Leu Phe Lys Phe Glu Val
1420                1425                1430                1435

ACA GCT ACT GAC ACG GCC GGC GCT CAG GAC CGC ACC GAC GTC ACC GTG       4549
Thr Ala Thr Asp Thr Ala Gly Ala Gln Asp Arg Thr Asp Val Thr Val
            1440                1445                1450

TAC GTG GTA TCC TCG CAG AAC CGC GTC TAC TTC GTG TTC GTC AAC ACG       4597
Tyr Val Val Ser Ser Gln Asn Arg Val Tyr Phe Val Phe Val Asn Thr
            1455                1460                1465

CTG CAA CAG GTC GAA GAC AAC AGA GAC TTT ATC GCG GAC ACC TTC AGC       4645
Leu Gln Gln Val Glu Asp Asn Arg Asp Phe Ile Ala Asp Thr Phe Ser
            1470                1475                1480

GCT GGG TTC AAC ATG ACC TGC AAC ATC GAC CAA GTG GTG CCC GCT AAC       4693
Ala Gly Phe Asn Met Thr Cys Asn Ile Asp Gln Val Val Pro Ala Asn
        1485                1490                1495

GAC CCC GTC ACC GGC GTG GCG CTG GAG CAC AGC ACG CAG ATG GCG GCC       4741
Asp Pro Val Thr Gly Val Ala Leu Glu His Ser Thr Gln Met Ala Ala
1500                1505                1510                1515

ACT TCA TAC GGG ACA ACG TAC CCG TAC TCG CTG ATG AGA TAGACAGATC        4790
Thr Ser Tyr Gly Thr Thr Tyr Pro Tyr Ser Leu Met Arg
            1520                1525

CGTAGTGACC TAGTCCTCCT GAGCTCGATA CAAACAACGC TGGCGGCGCG ATCGTGGTGT    4850

TGCAGGACTT GTTGACCAAC TCCAGCCCGG ACTTCGGCGC CTGACTCGAG CCTGCACGGT    4910

GTACGTCTGG CCTCACTGTC TGCTGTGCTC GGTTTCATGT GCCTTGTGCT ACTGCTTACC    4970

TTCATCATCA GGACTAGAGC GCTAAACCGA CGGTTGGAAG CCCTGTCGAT GACGAAGTAC    5030

GGCTCACTGG ACTCTGGATT GAACCGCGCC GGCATCGCCG CCCCCGGCAC CAACAAACAC    5090

ACTGTGGAAG GCTCCAACCC TATCTTCAAT GAAGCAATAA AGACGCCAGA TTTAGATGCC    5150

ATTAGCGAGG GTTCCAACGA CTCTGATCTG ATCGGCATCG AAGATCTTGC GCACTTTGGC    5210

AACGTCTTCA TGGATCCTGA GGTGAACGAA AAGGCAAATG GTTATCCCGA AGTCGCAAAC    5270

CACAACAACA ACTTCGCTTT CAACCCGACT CCCTTCTCGC CTGAGTTCGT TAACGGACAG    5330

TTCAGAAAGA TCTAGAAGAT AACAACACTA GTTAAGATCA TTAATTTTGG AGTTTGGAAT    5390

TAAGATTTTT GAAGGATAG TTGTGATAAG CCTGTGATTT TTAAAACTGT AATTGAAAAA    5450

AAAAATTGAG ACCTCCATTT AAGCTCTTGC TCTCATCTCA TCAAATTTTA TAAAATGCCA    5510

TTAGTCATTA AGATACTCGA TTTAATTTAA GATTATTTAA GATATTATGT AAAATAAATA    5570

TATTGTC                                                             5577
```

(2) INFORMATION FOR SEQ ID NO:2:

(i) SEQUENCE CHARACTERISTICS:
        (A) LENGTH: 1528 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Val Asp Val Arg Ile Ala Ala Phe Leu Leu Val Phe Ile Ala
 1               5                  10                  15

Pro Ala Val Leu Ala Gln Glu Arg Cys Gly Tyr Met Thr Ala Ile Pro
                20                  25                  30

Arg Leu Pro Arg Pro Asp Asn Leu Pro Val Leu Asn Phe Glu Gly Gln
            35                  40                  45

Thr Trp Ser Gln Arg Pro Leu Leu Pro Ala Pro Glu Arg Asp Asp Leu
        50                  55                  60

Cys Met Asp Ala Tyr His Val Ile Thr Ala Asn Leu Gly Thr Gln Val
 65                  70                  75                  80

Ile Tyr Met Asp Glu Glu Ile Glu Asp Glu Ile Thr Ile Ala Ile Leu
                 85                 90                  95

Asn Tyr Asn Gly Pro Ser Thr Pro Phe Ile Glu Leu Pro Phe Leu Ser
                100                 105                 110

Gly Ser Tyr Asn Leu Leu Met Pro Val Ile Arg Arg Val Asp Asn Gly
            115                 120                 125

Ser Ala Ser His His Ala Arg Gln His Tyr Glu Leu Pro Gly Met
130                 135                 140

Gln Gln Tyr Met Phe Asn Val Arg Val Asp Gly Gln Ser Leu Val Ala
145                 150                 155                 160

Gly Val Ser Leu Ala Ile Val Asn Ile Asp Asp Asn Ala Pro Ile Ile
                165                 170                 175

Gln Asn Phe Glu Pro Cys Arg Val Pro Glu Leu Gly Glu Pro Gly Leu
                180                 185                 190

Thr Glu Cys Thr Tyr Gln Val Ser Asp Ala Asp Gly Arg Ile Ser Thr
                195                 200                 205

Glu Phe Met Thr Phe Arg Ile Asp Ser Val Arg Gly Asp Glu Glu Thr
                210                 215                 220

Phe Tyr Ile Glu Arg Thr Asn Ile Pro Asn Gln Trp Met Trp Leu Asn
225                 230                 235                 240

Met Thr Ile Gly Val Asn Thr Ser Leu Asn Phe Val Thr Ser Pro Leu
                245                 250                 255

His Ile Phe Ser Val Thr Ala Leu Asp Ser Leu Pro Asn Thr His Thr
                260                 265                 270

Val Thr Met Met Val Gln Val Ala Asn Val Asn Ser Arg Pro Pro Arg
                275                 280                 285

Trp Leu Glu Ile Phe Ala Val Gln Gln Phe Glu Glu Lys Ser Tyr Gln
            290                 295                 300

Asn Phe Thr Val Arg Ala Ile Asp Gly Asp Thr Glu Ile Asn Met Pro
305                 310                 315                 320

Ile Asn Tyr Arg Leu Ile Thr Asn Glu Glu Asp Thr Phe Phe Ser Ile
                325                 330                 335

Glu Ala Leu Pro Gly Gly Lys Ser Gly Ala Val Phe Leu Val Ser Pro
                340                 345                 350

Ile Asp Arg Asp Thr Leu Gln Arg Glu Val Phe Pro Leu Thr Ile Val
                355                 360                 365

Ala Tyr Lys Tyr Asp Glu Glu Ala Phe Ser Ser Thr Asn Val Val
                370                 375                 380

Ile Ile Val Thr Asp Ile Asn Asp Gln Arg Pro Glu Pro Ile His Lys
385                 390                 395                 400
```

-continued

```
Glu Tyr Arg Leu Ala Ile Met Glu Thr Pro Leu Thr Leu Asn Phe
                405                 410                 415

Asp Lys Glu Phe Gly Phe His Asp Lys Asp Leu Gly Gln Asn Ala Gln
                420                 425                 430

Tyr Thr Val Arg Leu Glu Ser Val Asp Pro Pro Gly Ala Ala Glu Ala
                435                 440                 445

Phe Tyr Ile Ala Pro Glu Val Gly Tyr Gln Arg Gln Thr Phe Ile Met
450                             455                 460

Gly Thr Leu Asn His Ser Met Leu Asp Tyr Glu Val Pro Glu Phe Gln
465                 470                 475                 480

Ser Ile Thr Ile Arg Val Ala Thr Asp Asn Asp Thr Arg His
                485                 490                 495

Val Gly Val Ala Leu Val His Ile Asp Leu Ile Asn Trp Asn Asp Glu
                500                 505                 510

Gln Pro Ile Phe Glu His Ala Val Gln Thr Val Thr Phe Asp Glu Thr
                515                 520                 525

Glu Gly Glu Gly Phe Phe Val Ala Lys Ala Val Ala His Asp Arg Asp
                530                 535                 540

Ile Gly Asp Val Val Glu His Thr Leu Leu Gly Asn Ala Val Asn Phe
545                 550                 555                 560

Leu Thr Ile Asp Lys Leu Thr Gly Asp Ile Arg Val Ser Ala Asn Asp
                565                 570                 575

Ser Phe Asn Tyr His Arg Glu Ser Glu Leu Phe Val Gln Val Arg Ala
                580                 585                 590

Thr Asp Thr Leu Gly Glu Pro Phe His Thr Ala Thr Ser Gln Leu Val
                595                 600                 605

Ile Arg Leu Asn Asp Ile Asn Asn Thr Pro Pro Thr Leu Arg Leu Pro
                610                 615                 620

Arg Gly Ser Pro Gln Val Glu Asn Val Pro Asp Gly His Val Ile
625                 630                 635                 640

Thr Gln Glu Leu Arg Ala Thr Asp Pro Asp Thr Thr Ala Asp Leu Arg
                645                 650                 655

Phe Glu Ile Asn Trp Asp Thr Ser Phe Ala Thr Lys Gln Gly Arg Gln
                660                 665                 670

Ala Asn Pro Asp Glu Phe Arg Asn Cys Val Glu Ile Glu Thr Ile Phe
                675                 680                 685

Pro Glu Ile Asn Asn Arg Gly Leu Ala Ile Gly Arg Val Val Ala Arg
690                 695                 700

Glu Ile Arg His Asn Val Thr Ile Asp Tyr Glu Glu Phe Glu Val Leu
705                 710                 715                 720

Ser Leu Thr Val Arg Val Arg Asp Leu Asn Thr Val Tyr Gly Asp Asp
                725                 730                 735

Tyr Asp Glu Ser Met Leu Thr Ile Thr Ile Asp Met Asn Asp Asn
                740                 745                 750

Ala Pro Val Trp Val Glu Gly Thr Leu Glu Gln Asn Phe Arg Val Arg
                755                 760                 765

Glu Met Ser Ala Gly Gly Leu Val Val Gly Ser Val Arg Ala Asp Asp
                770                 775                 780

Ile Asp Gly Pro Leu Tyr Asn Gln Val Arg Tyr Thr Ile Phe Pro Arg
785                 790                 795                 800

Glu Asp Thr Asp Lys Asp Leu Ile Met Ile Asp Phe Leu Thr Gly Gln
                805                 810                 815

Ile Ser Val Asn Thr Ser Gly Ala Ile Asp Ala Asp Thr Pro Pro Arg
                820                 825                 830
```

-continued

```
Phe His Leu Tyr Tyr Thr Val Val Ala Ser Asp Arg Cys Ser Thr Glu
            835                 840                 845

Asp Pro Ala Asp Cys Pro Pro Asp Pro Thr Tyr Trp Glu Thr Glu Gly
    850                 855                 860

Asn Ile Thr Ile His Ile Thr Asp Thr Asn Asn Lys Val Pro Gln Ala
865                 870                 875                 880

Glu Thr Thr Lys Phe Asp Thr Val Val Tyr Ile Tyr Glu Asn Ala Thr
                885                 890                 895

His Leu Asp Glu Val Val Thr Leu Ile Ala Ser Asp Leu Asp Arg Asp
            900                 905                 910

Glu Ile Tyr His Thr Val Ser Tyr Val Ile Asn Tyr Ala Val Asn Pro
        915                 920                 925

Arg Leu Met Asn Phe Phe Ser Val Asn Arg Glu Thr Gly Leu Val Tyr
    930                 935                 940

Val Asp Tyr Glu Thr Gln Gly Ser Gly Glu Val Leu Asp Arg Asp Gly
945                 950                 955                 960

Asp Glu Pro Thr His Arg Ile Phe Phe Asn Leu Ile Asp Asn Phe Met
                965                 970                 975

Gly Glu Gly Glu Gly Asn Arg Asn Gln Asn Asp Thr Glu Val Leu Val
            980                 985                 990

Ile Leu Leu Asp Val Asn Asp Asn Ala Pro Glu Leu Pro Pro Pro Ser
        995                 1000                1005

Glu Leu Ser Trp Thr Ile Ser Glu Asn Leu Lys Gln Gly Val Arg Leu
    1010                1015                1020

Glu Pro His Ile Phe Ala Pro Asp Arg Asp Glu Pro Asp Thr Asp Asn
1025                1030                1035                1040

Ser Arg Val Gly Tyr Glu Ile Leu Asn Leu Ser Thr Glu Arg Asp Ile
                1045                1050                1055

Glu Val Pro Glu Leu Phe Val Met Ile Gln Ile Ala Asn Val Thr Gly
            1060                1065                1070

Glu Leu Glu Thr Ala Met Asp Leu Lys Gly Tyr Trp Gly Thr Tyr Ala
        1075                1080                1085

Ile His Ile Arg Ala Phe Asp His Gly Ile Pro Gln Met Ser Met Asn
    1090                1095                1100

Glu Thr Tyr Glu Leu Ile Ile His Pro Phe Asn Tyr Tyr Ala Pro Glu
1105                1110                1115                1120

Phe Val Phe Pro Thr Asn Asp Ala Val Ile Arg Leu Ala Arg Glu Arg
                1125                1130                1135

Ala Val Ile Asn Gly Val Leu Ala Thr Val Asn Gly Glu Phe Leu Glu
            1140                1145                1150

Arg Ile Ser Ala Thr Asp Pro Asp Gly Leu His Ala Gly Val Val Thr
        1155                1160                1165

Phe Gln Val Val Gly Asp Glu Ser Gln Arg Tyr Phe Gln Val Val
    1170                1175                1180

Asn Asp Gly Glu Asn Leu Gly Ser Leu Arg Leu Leu Gln Ala Val Pro
1185                1190                1195                1200

Glu Glu Ile Arg Glu Phe Arg Ile Thr Ile Arg Ala Thr Asp Gln Gly
                1205                1210                1215

Thr Asp Pro Gly Pro Leu Ser Thr Asp Met Thr Phe Arg Val Val Phe
            1220                1225                1230

Val Pro Thr Gln Gly Glu Pro Arg Phe Ala Ser Ser Glu His Ala Val
        1235                1240                1245
```

```
Ala Phe Ile Glu Lys Ser Ala Gly Met Glu Ser His Gln Leu Pro
            1250                1255                1260
Leu Ala Gln Asp Ile Lys Asn His Leu Cys Glu Asp Asp Cys His Ser
1265                1270                1275                1280
Ile Tyr Tyr Arg Ile Ile Asp Gly Asn Ser Glu Gly His Phe Gly Leu
                1285                1290                1295
Asp Pro Val Arg Asn Arg Leu Phe Leu Lys Lys Glu Leu Ile Arg Glu
            1300                1305                1310
Gln Ser Ala Ser His Thr Leu Gln Val Ala Ala Ser Asn Ser Pro Asp
        1315                1320                1325
Gly Gly Ile Pro Leu Pro Ala Ser Ile Leu Thr Val Thr Val
    1330                1335                1340
Arg Glu Ala Asp Pro Arg Pro Val Phe Val Arg Glu Leu Tyr Thr Ala
1345                1350                1355                1360
Gly Ile Ser Thr Ala Asp Ser Ile Gly Arg Glu Leu Leu Arg Leu His
            1365                1370                1375
Ala Thr Gln Ser Glu Gly Ser Ala Ile Thr Tyr Ala Ile Asp Tyr Asp
            1380                1385                1390
Thr Met Val Val Asp Pro Ser Leu Glu Ala Val Arg Gln Ser Ala Phe
        1395                1400                1405
Val Leu Asn Ala Gln Thr Gly Val Leu Thr Leu Asn Ile Gln Pro Thr
            1410                1415                1420
Ala Thr Met His Gly Leu Phe Lys Phe Glu Val Thr Ala Thr Asp Thr
1425                1430                1435                1440
Ala Gly Ala Gln Asp Arg Thr Asp Val Thr Val Tyr Val Val Ser Ser
            1445                1450                1455
Gln Asn Arg Val Tyr Phe Val Phe Val Asn Thr Leu Gln Gln Val Glu
            1460                1465                1470
Asp Asn Arg Asp Phe Ile Ala Asp Thr Phe Ser Ala Gly Phe Asn Met
            1475                1480                1485
Thr Cys Asn Ile Asp Gln Val Val Pro Ala Asn Asp Pro Val Thr Gly
            1490                1495                1500
Val Ala Leu Glu His Ser Thr Gln Met Ala Ala Thr Ser Tyr Gly Thr
1505                1510                1515                1520
Thr Tyr Pro Tyr Ser Leu Met Arg
            1525

(2) INFORMATION FOR SEQ ID NO:3:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:3:

Glu Trp Val Met Pro Pro Ile Phe Val Pro Glu Asn Gly Lys Gly Pro
1               5                   10                  15
Phe Pro Gln Arg Leu Asn Gln Leu Lys Ser Asn Lys Asp Arg Gly Thr
            20                  25                  30
Lys Ile Phe Tyr Tyr Ser Ile Thr Gly Pro Gly Ala Asp Ser Pro Pro
        35                  40                  45
Glu Gly Val Phe Thr Ile Glu Lys Glu Ser Gly Trp Leu Leu Leu His
    50                  55                  60
Met Pro Leu Asp Arg Glu Lys Ile Val Lys Tyr Glu Leu Tyr Gly His
65                  70                  75                  80
```

```
Ala Val Ser Glu Asn Gly Ala Ser Val Glu Pro Met Asn Ile Ser
                85                  90                  95

Ile Ile Val Thr Asp Gln Asn Asp Asn Lys Pro
               100                 105

(2) INFORMATION FOR SEQ ID NO:4:

(i) SEQUENCE CHARACTERISTICS:
        (A) LENGTH: 105 amino acids
        (B) TYPE: amino acid
        (C) STRANDEDNESS: single
        (D) TOPOLOGY: linear (xi) SEQUENCE DESCRIPTION: SEQ ID NO:4:

Glu Asp Thr Val Tyr Ser Phe Asp Ile Asp Glu Asn Ala Gln Arg Gly
1               5                  10                  15

Tyr Gln Val Gly Gln Ile Val Ala Arg Asp Ala Asp Leu Gly Gln Asn
                20                  25                  30

Ala Gln Leu Ser Tyr Gly Val Val Ser Asp Trp Ala Asn Asp Val Phe
                35                  40                  45

Ser Leu Asn Pro Gln Thr Gly Met Leu Thr Leu Thr Ala Arg Leu Asp
                50                  55                  60

Tyr Glu Glu Val Gln His Tyr Ile Leu Ile Val Gln Ala Gln Asp Asn
65                  70                  75                  80

Gly Gln Pro Ser Leu Ser Thr Thr Ile Thr Val Tyr Cys Asn Val Leu
                85                  90                  95

Asp Leu Asn Asp Asn Ala Pro Ile Phe
               100                 105

(2) INFORMATION FOR SEQ ID NO:5:

(i) SEQUENCE CHARACTERISTICS:
        (A) LENGTH: 93 amino acids
        (B) TYPE: amino acid
        (C) STRANDEDNESS: single
        (D) TOPOLOGY: linear (xi) SEQUENCE DESCRIPTION: SEQ ID NO:5:

Ala Ser Pro Val Ile Thr Leu Ala Ile Pro Glu Asn Thr Asn Ile Gly
1               5                  10                  15

Ser Leu Phe Pro Ile Pro Leu Ala Ser Asp Arg Asp Ala Asn Glu Leu
                20                  25                  30

Gln Val Ala Glu Asp Gln Glu Glu Lys Gln Pro Gln Leu Ile Val Met
                35                  40                  45

Gly Asn Leu Asp Arg Glu Arg Trp Asp Ser Tyr Asp Leu Thr Ile Lys
                50                  55                  60

Val Gln Asp Gly Gly Ser Pro Pro Arg Ala Thr Ser Ala Leu Leu Arg
65                  70                  75                  80

Val Thr Val Leu Asp Thr Asn Asp Asn Ala Pro Lys Phe
                85                  90

(2) INFORMATION FOR SEQ ID NO:6:

(i) SEQUENCE CHARACTERISTICS:
        (A) LENGTH: 106 amino acids
        (B) TYPE: amino acid
        (C) STRANDEDNESS: single
        (D) TOPOLOGY: linear (xi) SEQUENCE DESCRIPTION: SEQ ID NO:6:
```

Ile Val Thr Glu Asn Ile Trp Lys Ala Pro Lys Pro Val Glu Met Val
1               5                   10                  15

Glu Asn Ser Thr Pro His Pro Ile Lys Ile Thr Gln Val Arg Trp Asn
                20                  25                  30

Asp Pro Gly Ala Gln Tyr Ser Leu Val Asp Lys Glu Lys Leu Pro Arg
            35                  40                  45

Phe Pro Phe Ser Ile Asp Gln Glu Gly Asp Ile Tyr Val Thr Pro Leu
50                      55                  60

Asp Arg Glu Lys Asp Ala Tyr Val Phe Tyr Ala Val Ala Lys Asp
65                  70                  75                  80

Glu Tyr Gly Lys Pro Leu Ser Tyr Pro Leu Glu Ile His Val Lys Val
                85                  90                  95

Lys Asp Ile Asn Asp Asn Pro Pro Thr Cys
                100                 105

(2) INFORMATION FOR SEQ ID NO:7:

(i) SEQUENCE CHARACTERISTICS:
        (A) LENGTH: 105 amino acids
        (B) TYPE: amino acid
        (C) STRANDEDNESS: single
        (D) TOPOLOGY: linear (xi) SEQUENCE DESCRIPTION: SEQ ID NO:7:

Ile Thr Ala Asn Leu Gly Thr Gln Val Ile Tyr Met Asp Glu Glu Ile
1               5                   10                  15

Glu Asp Glu Ile Thr Ile Ala Ile Leu Asn Tyr Asn Gly Pro Ser Thr
                20                  25                  30

Pro Phe Ile Glu Leu Pro Phe Leu Ser Gly Ser Tyr Asn Leu Leu Met
            35                  40                  45

Pro Val Ile Arg Arg Val Asp Asn Gly Ser Ala Ser His His His Ala
50                  55                  60

Arg Gln His Tyr Glu Leu Pro Gly Met Gln Gln Tyr Met Phe Asn Val
65                  70                  75                  80

Arg Val Asp Gly Gln Ser Leu Val Ala Gly Val Ser Leu Ala Ile Val
                85                  90                  95

Asn Ile Asp Asp Asn Ala Pro Ile Ile
                100                 105

(2) INFORMATION FOR SEQ ID NO:8:

(i) SEQUENCE CHARACTERISTICS:
        (A) LENGTH: 113 amino acids
        (B) TYPE: amino acid
        (C) STRANDEDNESS: single
        (D) TOPOLOGY: linear (xi) SEQUENCE DESCRIPTION: SEQ ID NO:8:

Gln Asn Phe Glu Pro Cys Arg Val Pro Glu Leu Gly Glu Pro Gly Leu
1               5                   10                  15

Thr Glu Cys Thr Tyr Gln Val Ser Asp Ala Asp Gly Arg Ile Ser Thr
                20                  25                  30

Glu Phe Met Thr Phe Arg Ile Asp Ser Val Arg Gly Asp Glu Glu Thr
            35                  40                  45

Phe Tyr Ile Glu Arg Thr Asn Ile Pro Asn Gln Trp Met Trp Leu Asn
50                  55                  60

Met Thr Ile Gly Val Asn Thr Ser Leu Asn Phe Val Thr Ser Pro Leu
65                  70                  75                  80

```
His Ile Phe Ser Val Thr Ala Leu Asp Ser Leu Pro Asn Thr His Thr
                85                  90                  95

Val Thr Met Met Val Gln Val Ala Asn Val Asn Ser Arg Pro Pro Arg
            100                 105                 110

Trp (2) INFORMATION FOR SEQ ID NO:9:

(i) SEQUENCE CHARACTERISTICS:
        (A) LENGTH: 106 amino acids
        (B) TYPE: amino acid
        (C) STRANDEDNESS: single
        (D) TOPOLOGY: linear (xi) SEQUENCE DESCRIPTION: SEQ ID NO:9:

Leu Glu Ile Phe Ala Val Gln Gln Phe Glu Glu Lys Ser Tyr Gln Asn
1               5                  10                  15

Phe Thr Val Arg Ala Ile Asp Gly Asp Thr Glu Ile Asn Met Pro Ile
                20                  25                  30

Asn Tyr Arg Leu Ile Thr Asn Glu Glu Asp Thr Phe Phe Ser Ile Glu
            35                  40                  45

Ala Leu Pro Gly Gly Lys Ser Gly Ala Val Phe Leu Val Ile Asp Arg
50                  55                  60

Asp Thr Leu Gln Arg Glu Val Phe Pro Leu Thr Ile Val Ala Tyr Lys
65                  70                  75                  80

Tyr Asp Glu Glu Ala Phe Ser Ser Thr Asn Val Val Ile Ile Val
                85                  90                  95

Thr Asp Ile Asn Asp Gln Arg Pro Glu Pro
            100                 105

(2) INFORMATION FOR SEQ ID NO:10:

(i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO:10:

Ile His Lys Glu Tyr Arg Leu Ala Ile Met Glu Glu Thr Pro Leu Thr
1               5                   10                  15

Leu Asn Phe Asp Lys Glu Phe Gly Phe His Asp Lys Asp Leu Gly Gln
                20                  25                  30

Asn Ala Gln Tyr Thr Val Arg Leu Glu Ser Val Asp Pro Pro Gly Ala
            35                  40                  45

Ala Glu Ala Phe Tyr Ile Ala Pro Glu Val Gly Tyr Gln Arg Gln Thr
50                  55                  60

Phe Ile Met Gly Thr Leu Asn His Ser Met Leu Asp Tyr Glu Val Pro
65                  70                  75                  80

Glu Phe Gln Ser Ile Thr Ile Arg Val Ala Thr Asp Asn Asn Asp
                85                  90                  95

Thr Arg His Val Gly Val Ala Leu Val His Ile Asp Leu Ile Asn Trp
            100                 105                 110

Asn Asp Glu Gln Pro Ile Phe
        115

(2) INFORMATION FOR SEQ ID NO:11:

(i) SEQUENCE CHARACTERISTICS:
        (A) LENGTH: 104 amino acids
```

```
            (B) TYPE: amino acid
            (C) STRANDEDNESS: single
            (D) TOPOLOGY: linear (xi) SEQUENCE DESCRIPTION: SEQ ID NO:11:

Glu His Ala Val Gln Thr Val Thr Phe Asp Glu Thr Glu Gly Glu Gly
1               5                   10                  15

Phe Phe Val Ala Lys Ala Val Ala His Asp Arg Asp Ile Gly Asp Val
            20                  25                  30

Val Glu His Thr Leu Leu Gly Asn Ala Val Asn Phe Leu Thr Ile Asp
        35                  40                  45

Lys Leu Thr Gly Asp Ile Arg Val Ser Ala Asn Asp Ser Phe Tyr His
    50                  55                  60

Arg Glu Ser Glu Leu Phe Val Gln Val Arg Ala Thr Asp Thr Leu Gly
65                  70                  75                  80

Gln Pro Phe His Thr Ala Thr Ser Gln Leu Val Ile Arg Leu Asn Asp
                85                  90                  95

Ile Asn Asn Thr Pro Pro Thr Leu
                100

(2) INFORMATION FOR SEQ ID NO:12:

(i) SEQUENCE CHARACTERISTICS:
        (A) LENGTH: 138 amino acids
        (B) TYPE: amino acid
        (C) STRANDEDNESS: single
        (D) TOPOLOGY: linear (xi) SEQUENCE DESCRIPTION: SEQ ID NO:12:

Arg Leu Pro Arg Gly Ser Pro Gln Val Glu Glu Asn Val Pro Asp Ala
1               5                   10                  15

His Val Ile Thr Gln Glu Leu Arg Ala Thr Asp Pro Asp Thr Thr Ala
            20                  25                  30

Asp Leu Arg Phe Glu Ile Asn Trp Asp Thr Ser Phe Ala Thr Lys Gln
            35                  40                  45

Gly Arg Gln Ala Asn Pro Asp Glu Phe Arg Asn Cys Val Glu Ile Glu
    50                  55                  60

Thr Ile Phe Phe Pro Glu Ile Asn Asn Ile Asn Asn Arg Gly Leu Ala
65                  70                  75                  80

Ile Gly Arg Val Val Ala Arg Glu Ile Arg His Asn Thr Ile Asp Tyr
                85                  90                  95

Glu Glu Phe Glu Val Leu Ser Leu Thr Val Arg Val Arg Asp Leu Asn
                100                 105                 110

Thr Val Tyr Gly Asp Asp Tyr Asp Glu Ser Met Leu Thr Ile Thr Ile
            115                 120                 125

Ile Asp Met Asn Asp Asn Ala Pro Val Trp
        130                 135

(2) INFORMATION FOR SEQ ID NO:13:

(i) SEQUENCE CHARACTERISTICS:
        (A) LENGTH: 124 amino acids
        (B) TYPE: amino acid
        (C) STRANDEDNESS: single
        (D) TOPOLOGY: linear (xi) SEQUENCE DESCRIPTION: SEQ ID NO:13:

Val Glu Gly Thr Leu Glu Gln Asn Phe Arg Val Arg Glu Met Ser Ala
1               5                   10                  15
```

```
Gly Gly Leu Val Val Gly Ser Val Arg Ala Asp Asp Ile Asp Gly Pro
            20                  25                  30

Leu Tyr Asn Gln Val Arg Tyr Thr Ile Phe Pro Arg Glu Asp Thr Asp
            35                  40                  45

Lys Asp Leu Ile Met Ile Glu Leu Pro His Gly Ser Asn Phe Arg Glu
 50                  55                  60

His Lys Arg Arg Ile Asp Ala Asn Thr Pro Pro Arg Phe His Leu Tyr
 65                  70                  75                  80

Tyr Thr Val Val Ala Ser Asp Arg Cys Ser Thr Glu Asp Pro Ala Asp
                     85                  90                  95

Cys Pro Pro Asp Pro Tyr Tyr Trp Glu Thr Glu Gly Asn Ile Thr Ile
                100                 105                 110

His Ile Thr Asp Thr Asn Asn Lys Val Pro Gln Ala
            115                 120

(2) INFORMATION FOR SEQ ID NO:14:

(i) SEQUENCE CHARACTERISTICS:
        (A) LENGTH: 122 amino acids
        (B) TYPE: amino acid
        (C) STRANDEDNESS: single
        (D) TOPOLOGY: linear (xi) SEQUENCE DESCRIPTION: SEQ ID NO:14:

Glu Thr Thr Lys Phe Asp Thr Val Val Tyr Ile Tyr Glu Asn Ala Thr
 1                   5                  10                  15

His Leu Asp Glu Val Val Thr Leu Ile Ala Ser Asp Leu Asp Arg Asp
            20                  25                  30

Glu Ile Tyr His Met Val Ser Tyr Val Ile Asn Tyr Ala Val Asn Pro
            35                  40                  45

Arg Leu Met Asn Phe Phe Ser Val Asn Arg Glu Thr Gly Leu Val Tyr
 50                  55                  60

Val Asp Tyr Glu Thr Gln Gly Ser Gly Leu Ala Arg Asp Gly Asp Glu
 65                  70                  75                  80

Pro Thr His Arg Ile Phe Phe Asn Leu Ile Asp Asn Phe Met Gly Glu
                     85                  90                  95

Gly Glu Gly Asn Arg Asn Gln Asn Asp Thr Glu Val Leu Val Ile Leu
                100                 105                 110

Leu Asp Val Asn Asp Asn Ala Pro Glu Leu
            115                 120

(2) INFORMATION FOR SEQ ID NO:15:

(i) SEQUENCE CHARACTERISTICS:
        (A) LENGTH: 146 amino acids
        (B) TYPE: amino acid
        (C) STRANDEDNESS: single
        (D) TOPOLOGY: linear (xi) SEQUENCE DESCRIPTION: SEQ ID NO:15:

Pro Pro Pro Ser Glu Leu Ser Trp Thr Ile Ser Glu Asn Leu Lys Gln
 1                   5                  10                  15

Gly Val Arg Leu Glu Pro His Ile Phe Ala Pro Asp Arg Asp Glu Pro
            20                  25                  30

Asp Thr Asp Asn Ser Arg Val Gly Tyr Glu Ile Leu Asn Leu Ser Thr
            35                  40                  45

Glu Arg Asp Ile Glu Val Pro Glu Leu Phe Val Met Ile Gln Ile Ile
 50                  55                  60
```

```
Ala Asn Val Thr Gly Tyr Glu Ile Leu Asn Leu Ser Thr Glu Arg Asp
 65                  70                  75                  80

Ile Glu Val Pro Glu Leu Phe Val Met Ile Gln Ile Ala Asn Val Thr
                 85                  90                  95

Gly Glu Leu Glu Thr Ala Met Asp Leu Lys Gly Tyr Trp Gly Thr Tyr
                100                 105                 110

Ala Ile Tyr Ile Leu Ala Phe Asp His Gly Ile Pro Gln Met Ser Met
            115                 120                 125

Asn Glu Thr Tyr Glu Leu Ile Ile His Pro Phe Asn Tyr Tyr Ala Pro
    130                 135                 140

Glu Phe
145

(2) INFORMATION FOR SEQ ID NO:16:

(i) SEQUENCE CHARACTERISTICS:
        (A) LENGTH: 120 amino acids
        (B) TYPE: amino acid
        (C) STRANDEDNESS: single
        (D) TOPOLOGY: linear (xi) SEQUENCE DESCRIPTION: SEQ ID NO:16:

Val Phe Pro Thr Asn Asp Ala Val Ile Arg Leu Ala Arg Glu Arg Ala
 1               5                  10                  15

Val Ile Asn Gly Val Leu Ala Thr Val Asn Gly Glu Phe Leu Glu Arg
             20                  25                  30

Ile Ser Ala Thr Asp Pro Asp Gly Leu His Ala Gly Val Val Thr Phe
         35                  40                  45

Gln Val Gly Asp Glu Glu Ser Gln Arg Tyr Phe Gln Val Val Asp Asn
 50                  55                  60

Asp Gly Glu Asn Leu Gly Ser Leu Arg Leu Leu Gln Ala Val Pro Glu
 65                  70                  75                  80

Glu Ile Arg Glu Phe Arg Ile Thr Ile Arg Ala Thr Asp Gln Gly Thr
                 85                  90                  95

Asp Pro Gly Pro Leu Ser Thr Asp Met Thr Phe Arg Val Val Phe Val
                100                 105                 110

Pro Thr Gln Gly Glu Pro Arg Phe
            115                 120

(2) INFORMATION FOR SEQ ID NO:17:

(i) SEQUENCE CHARACTERISTICS:
        (A) LENGTH: 112 amino acids
        (B) TYPE: amino acid
        (C) STRANDEDNESS: single
        (D) TOPOLOGY: linear (xi) SEQUENCE DESCRIPTION: SEQ ID NO:17:

Ala Ser Ser Glu His Ala Val Ala Phe Ile Glu Lys Ser Ala Gly Met
 1               5                  10                  15

Glu Glu Ser His Gln Leu Pro Leu Ala Gln Asp Ile Lys Asn His Leu
             20                  25                  30

Cys Glu Asp Asp Cys His Ser Ile Tyr Tyr Arg Ile Ile Asp Gly Asn
         35                  40                  45

Ser Glu Gly His Phe Gly Leu Asp Pro Val Arg Asn Arg Leu Phe Leu
 50                  55                  60

Lys Lys Glu Leu Ile Arg Glu Gln Ser Ala Ser His Thr Leu Gln Val
 65                  70                  75                  80
```

```
Ala Ala Ser Asn Ser Pro Asp Gly Gly Ile Pro Leu Pro Ala Ser Ile
                85                  90                  95

Leu Thr Val Thr Val Thr Val Arg Glu Ala Asp Pro Arg Pro Val Phe
            100                 105                 110

(2) INFORMATION FOR SEQ ID NO:18:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:18:

Met Leu Asp Tyr Glu Val Pro Glu Phe Gln Ser Ile Thr Ile Arg Val
1               5                  10                  15

Val Ala Thr Asp Asn Asn Asp Thr Arg His Val Gly Val Ala
            20                  25                  30

(2) INFORMATION FOR SEQ ID NO:19:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:19:

Met Xaa Glu Thr Tyr Glu Leu Ile Ile His Pro Phe Asn Tyr Tyr Ala
1               5                  10                  15

(2) INFORMATION FOR SEQ ID NO:20:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:20:

Met Xaa Xaa Xaa His Gln Leu Pro Leu Ala Gln Asp Ile Lys Asn His
1               5                  10                  15

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "This position is Phe/Pro"

(ix) FEATURE:
        (A) NAME/KEY: Modified-site
        (B) LOCATION: 3
        (D) OTHER INFORMATION: /note= "This position is Asn/Ile"

(ix) FEATURE:
        (A) NAME/KEY: Modified-site
        (B) LOCATION: 5
        (D) OTHER INFORMATION: /note= "This position is Arg/Tyr"

(ix) FEATURE:
        (A) NAME/KEY: Modified-site
        (B) LOCATION: 8
        (D) OTHER INFORMATION: /note= "This position is Ile/Gly"
```

(xi) SEQUENCE DESCRIPTION: SEQ ID NO:21:

Met Xaa Xaa Val Xaa Val Asp Xaa
1               5

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /note= "This position is Phe/His"

(ix) FEATURE:
        (A) NAME/KEY: Modified-site
        (B) LOCATION: 8
        (D) OTHER INFORMATION: /note= "This position is Arg/Asp"

(xi) SEQUENCE DESCRIPTION: SEQ ID NO:22:

Met Asn Phe Xaa Ser Val Asn Xaa Glu
1               5

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:23:

Ala Xaa Asp Xaa Asp
1               5

(2) INFORMATION FOR SEQ ID NO:24:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:24:

Asp Xaa Asn Asp Xaa Xaa Pro
1               5

(2) INFORMATION FOR SEQ ID NO:25:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "Alanine(A) or Valine(V)"

(xi) SEQUENCE DESCRIPTION: SEQ ID NO:25:

Xaa Xaa Asp Xaa Asp
1               5

(2) INFORMATION FOR SEQ ID NO:26:

```
        (i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:26:

Asp Xaa Asn Asp Asn
1               5
```